(12) United States Patent
Duncan

(10) Patent No.: US 10,676,506 B2
(45) Date of Patent: Jun. 9, 2020

(54) CRYSTALLINE BIS- AND TRIS-HYDROCHLORIDE SALT OF ELAMIPRETIDE

(71) Applicant: Stealth BioTherapeutics Corp., MC (MC)

(72) Inventor: Scott M. Duncan, Bedford, MA (US)

(73) Assignee: Stealth BioTherapeutics Corp., Monte Carlo (MC)

( * ) Notice: Subject to any disclaimer, the term of this patent is extended or adjusted under 35 U.S.C. 154(b) by 0 days.

(21) Appl. No.: 16/259,575

(22) Filed: Jan. 28, 2019

(65) Prior Publication Data

US 2019/0233474 A1    Aug. 1, 2019

Related U.S. Application Data

(60) Provisional application No. 62/656,649, filed on Apr. 12, 2018, provisional application No. 62/622,259, filed on Jan. 26, 2018.

(51) Int. Cl.
*C07K 7/00* (2006.01)
*C07K 5/11* (2006.01)
*C07K 1/14* (2006.01)

(52) U.S. Cl.
CPC .............. *C07K 5/1019* (2013.01); *C07K 1/14* (2013.01); *C07B 2200/13* (2013.01)

(58) Field of Classification Search
None
See application file for complete search history.

(56) References Cited

U.S. PATENT DOCUMENTS

| | | |
|---|---|---|
| 6,703,483 B1 | 3/2004 | Schiller |
| 7,498,297 B2 | 3/2009 | Szeto et al. |
| 7,576,061 B2 | 8/2009 | Szeto et al. |
| 7,718,620 B2 | 5/2010 | Szeto et al. |
| 7,732,398 B2 | 6/2010 | Szeto et al. |
| 8,404,646 B2 | 3/2013 | Schiller et al. |
| 8,957,030 B2 | 2/2015 | Szeto et al. |
| 9,345,738 B2 | 5/2016 | Wilson et al. |
| 9,549,963 B2 | 1/2017 | Liu et al. |
| 9,561,258 B2 | 2/2017 | Wilson |
| 9,636,378 B2 | 5/2017 | Wilson |
| 9,982,014 B2 | 5/2018 | Hirai et al. |
| 9,988,422 B2 | 6/2018 | Wilson et al. |
| 10,188,692 B2 | 1/2019 | Liu et al. |
| 10,188,693 B2 | 1/2019 | Wilson et al. |
| 10,221,213 B2 | 3/2019 | Wilson |
| 2013/0196921 A1 | 8/2013 | Wilson et al. |
| 2014/0093897 A1 | 4/2014 | Szeto et al. |
| 2015/0118315 A1 | 4/2015 | Wilson |
| 2016/0030501 A1 | 2/2016 | Borow et al. |
| 2016/0151446 A1 | 6/2016 | Wilson |
| 2016/0228491 A1 | 8/2016 | Wilson |
| 2016/0264623 A1* | 9/2016 | Hirai .................... C07K 5/1019 |
| 2017/0028015 A1 | 2/2017 | Borow et al. |
| 2017/0081363 A1 | 3/2017 | Wilson |
| 2017/0087204 A1 | 3/2017 | Wilson et al. |
| 2017/0240593 A1 | 8/2017 | Szeto et al. |
| 2018/0044378 A1 | 2/2018 | Duncan et al. |
| 2019/0022165 A1 | 1/2019 | Wilson |
| 2019/0022167 A1 | 1/2019 | Wilson |

FOREIGN PATENT DOCUMENTS

| | | |
|---|---|---|
| WO | WO-2014/134554 A1 | 9/2014 |
| WO | WO-2014/134562 A1 | 9/2014 |
| WO | WO-2014/185952 A1 | 11/2014 |
| WO | WO-2014/209905 A2 | 12/2014 |
| WO | WO-2014/210056 A1 | 12/2014 |
| WO | WO-2014/210062 A1 | 12/2014 |
| WO | WO-2015/009414 A1 | 1/2015 |
| WO | WO-2015/017781 A1 | 2/2015 |
| WO | WO-2015/017861 A1 | 2/2015 |
| WO | WO-2015/023680 A1 | 2/2015 |
| WO | WO-2015/100376 A1 | 7/2015 |
| WO | WO-2015/103577 A1 | 7/2015 |
| WO | WO-2015/134096 A1 | 9/2015 |
| WO | WO-2015/183988 A1 | 12/2015 |
| WO | WO-2015/183995 A2 | 12/2015 |
| WO | WO-2015/195737 A1 | 12/2015 |
| WO | WO-2016/004067 A1 | 1/2016 |
| WO | WO-2016/004093 A2 | 1/2016 |
| WO | WO-2016/029027 A2 | 2/2016 |
| WO | WO-2016/144905 A1 | 9/2016 |
| WO | WO-2016/209261 A1 | 12/2016 |
| WO | WO-2017/151886 A1 | 9/2017 |
| WO | WO-2017/156403 A1 | 9/2017 |
| WO | WO-2017/201433 A1 | 11/2017 |
| WO | WO-2018/034901 A1 | 2/2018 |
| WO | WO-2018/187400 A1 | 10/2018 |
| WO | WO-2018/223032 A1 | 12/2018 |

OTHER PUBLICATIONS

McPherson and Gavira, Acta Cryst. (2014). F70, 2-20.*

* cited by examiner

*Primary Examiner* — Jeanette M Lieb
(74) *Attorney, Agent, or Firm* — Foley Hoag LLP

(57) ABSTRACT

Disclosed are crystalline forms of the bis- and tris-(hydrochloride) salts of D-Arg-Tyr(2,6-DiMe)-Lys-Phe-$NH_2$, which is also known as MTP-131.

19 Claims, 10 Drawing Sheets

US 10,676,506 B2

CRYSTALLINE BIS- AND TRIS-HYDROCHLORIDE SALT OF ELAMIPRETIDE

RELATED APPLICATIONS

This application claims the benefit of priority to U.S. Provisional Patent Application No. 62/656,649, filed Apr. 12, 2018; and U.S. Provisional Patent Application No. 62/622,259, filed Jan. 26, 2018.

BACKGROUND

Through oxidative phosphorylation, mitochondria convert nutrients and oxygen into adenosine triphosphate (ATP), the chemical transporter of energy in most aerobic organisms. The electron transport chain (ETC) of mitochondria represents the primary source of ATP, as well as a source of reactive oxygen species (ROS). Mitochondrial dysfunction results in less ATP production and, as a result, insufficient energy to maintain the cell. Such dysfunction also results in excessive ROS production, spiraling cellular injury, and ultimately apoptosis of the cell. Mitochondrial dysfunction, is a key element believed to be at the root of a variety of serious, debilitating diseases.

Natural antioxidants, such as coenzyme Q and vitamin E, have been shown to provide some protection of the cell from damage induced by elevated ROS levels associated with mitochondrial dysfunction. However, antioxidants or oxygen scavengers have also been shown to reduce ROS to unhealthy levels and may not reach the ETC in sufficient concentrations to correct the mitochondrial imbalance. Therefore, there is a need for novel compounds that can selectively target the ETC, restore efficient oxidative phosphorylation, and, thereby, address mitochondrial disease and dysfunction.

Elamipretide (MTP-131) is a mitochondria-targeting compound with therapeutic potential for treating diseases associated with mitochondrial dysfunction. Because of the potential therapeutic applications of the compound, there exists a need to develop new crystalline solid forms.

SUMMARY

Disclosed are crystalline forms of the bis and tris-(hydrochloride) salt of D-Arg-Tyr(2,6-DiMe)-Lys-Phe-NH2, which is also known as MTP-131.

DETAILED DESCRIPTION

The present invention relates to salts of Compound (I):

(I)

[Chemical structure of Compound (I)]

which compound is also known as MTP-131 and D-Arg-Tyr(2,6-DiMe)-Lys-Phe-NH$_2$. Compound (I) has been shown to affect the mitochondrial disease process by helping to protect organs from oxidative damage caused by excess ROS production and restoring normal ATP production.

A crystalline form of a salt of Compound (I) can be used to modulate/improve the physicochemical properties of the compound, including but not limited to solid state properties (e.g., crystallinity, hygroscopicity, melting point, or hydration), pharmaceutical properties (e.g., solubility/dissolution rate, stability, or compatibility), as well as crystallization characteristics (e.g., purity, yield, or morphology).

In certain embodiments, the present invention provides a pharmaceutical preparation comprising a crystalline salt of Compound (I) and one or more pharmaceutically acceptable excipients. In certain embodiments, the pharmaceutical preparations may be for use in treating or preventing a condition or disease as described herein.

In certain embodiments, a polymorph of the crystalline salt is characterized by powder X-ray diffraction (XRD). $\theta$ represents the diffraction angle, measured in degrees. In certain embodiments, the diffractometer used in XRD measures the diffraction angle as two times the diffraction angle $\theta$. Thus, in certain embodiments, the diffraction patterns described herein refer to X-ray intensity measured against angle $2\theta$.

In certain embodiments, a crystalline salt of Compound (I) is not solvated (e.g., the crystal lattice does not comprise molecules of a solvent). In certain alternative embodiments, a crystalline salt of Compound (I) is solvated. In some cases, the solvent is water.

Figure 1:
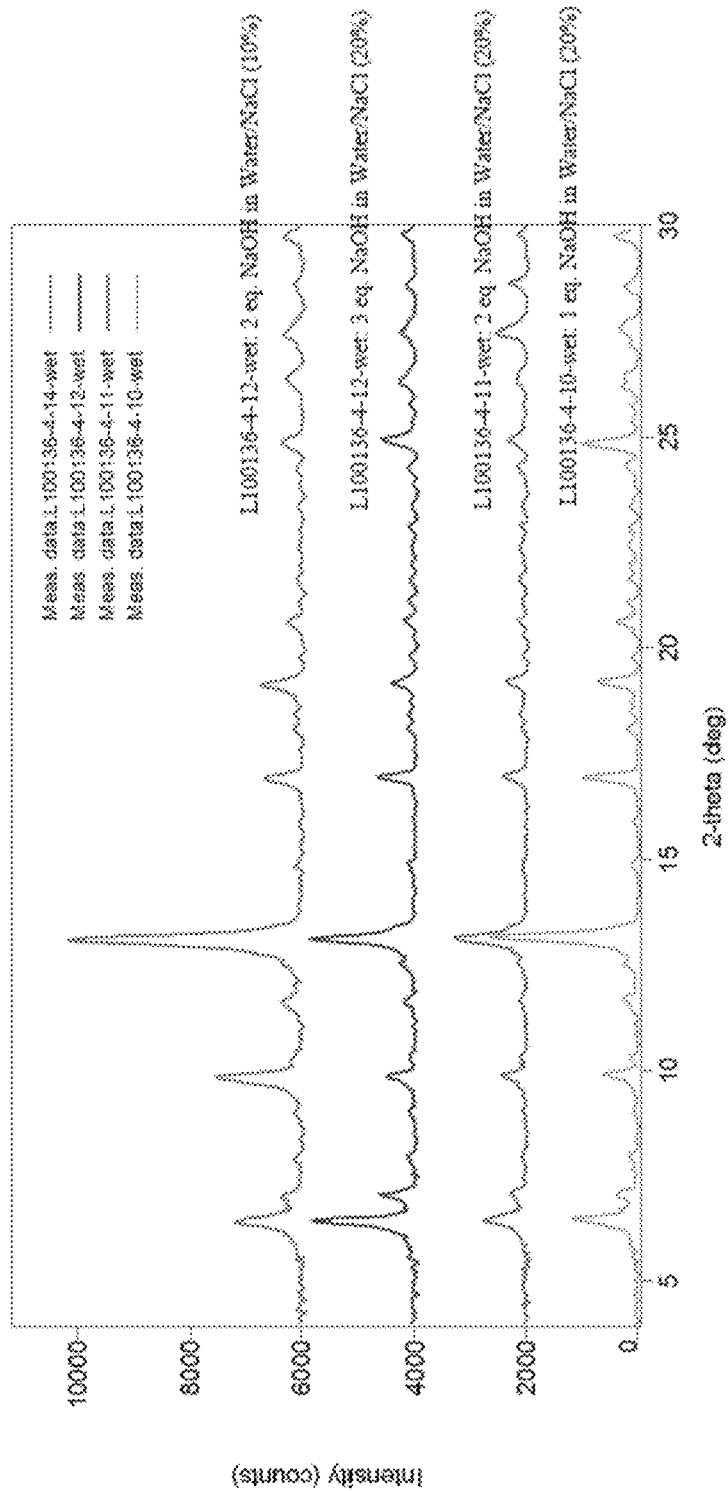
FIG. 1 depicts XRPD patterns of the crystalline solids observed when one or more equiv. of sodium hydroxide is added to aqueous sodium chloride solutions of Compound (I).
Figure 2:
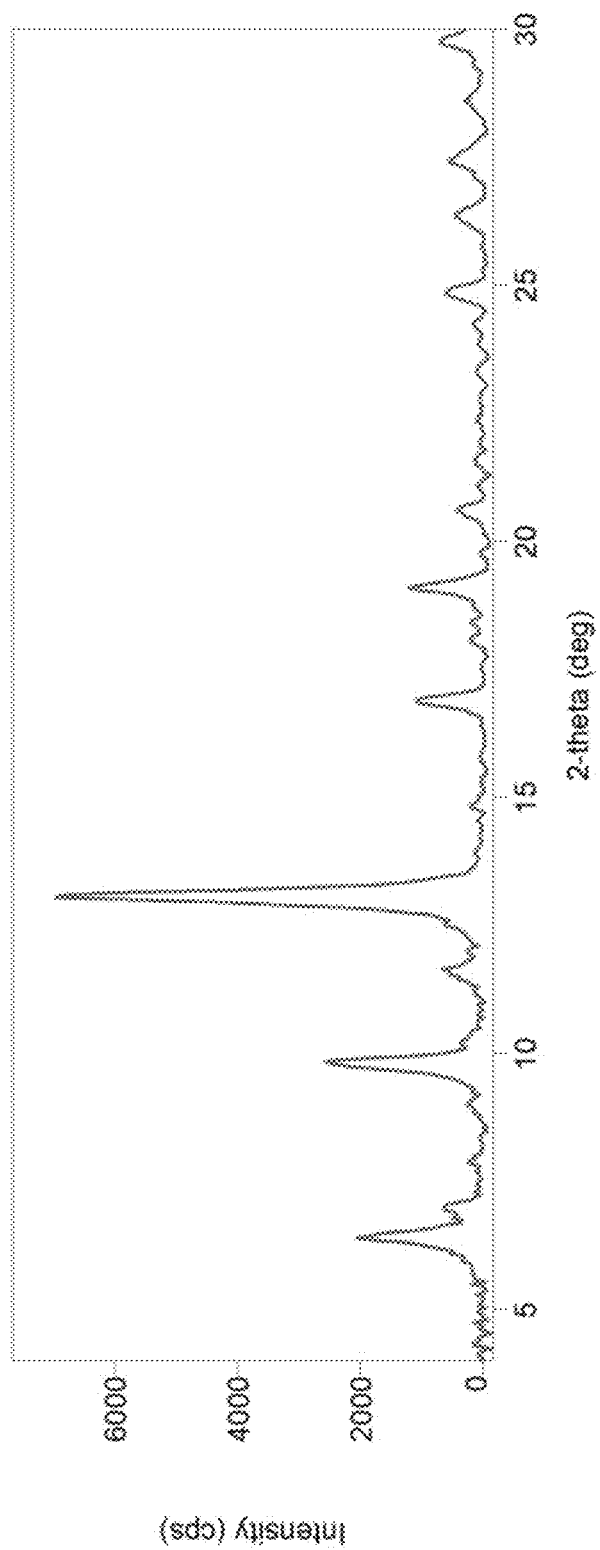
FIG. 2 is XRPD Pattern A of the crystalline bis-HCl salt of Compound (I).

In one aspect, the invention features a crystalline form of Compound (I) which has characteristic peaks in the powder X-ray diffraction (XRPD) pattern as shown in FIG. 2.

In another aspect, the invention features a crystalline form of Compound (I) which has characteristic peaks in the powder X-ray diffraction (XRPD) pattern at values of two theta (° 2θ) as shown in Table 2.

The relative intensity, as well as the two theta value, of each peak in Table 2, as well as in FIG. 2, may change or shift under certain conditions, although the crystalline form is the same. One of ordinary skill in the art should be able to determine readily whether a given crystalline form is the same crystalline form as described in Table 2, as well as in FIG. 2, by comparing their XRPD data.

In yet another aspect, the invention features a crystalline form of a bis-hydrochloride salt of Compound (I) which has characteristic peaks in the powder X-ray diffraction (XRPD) pattern as shown in FIG. 2.

In yet another aspect, the invention features a crystalline form of a bis-hydrochloride salt of Compound (I) which has characteristic peaks in the powder X-ray diffraction (XRPD) pattern as shown in Table 2.

In another aspect, the invention features a crystalline form of a bis-hydrochloride salt of Compound (I) which has characteristic peaks in the powder X-ray diffraction (XRPD) pattern at values of two theta (° 2θ) of 6.4, 9.8, 13.1, 16.9, 19.1, and 29.7.

In another aspect, the invention features a crystalline form of a bis-hydrochloride salt of Compound (I) which has characteristic peaks in the powder X-ray diffraction (XRPD) pattern at values of two theta (° 2θ) of 6.4, 7.0, 7.9, 9.1, 9.8, 10.2, 11.7, 13.1, 16.9, 19.1, 20.6, 24.2, 24.8, 26.3, 27.4, 28.6, and 29.7.

Figure 3:
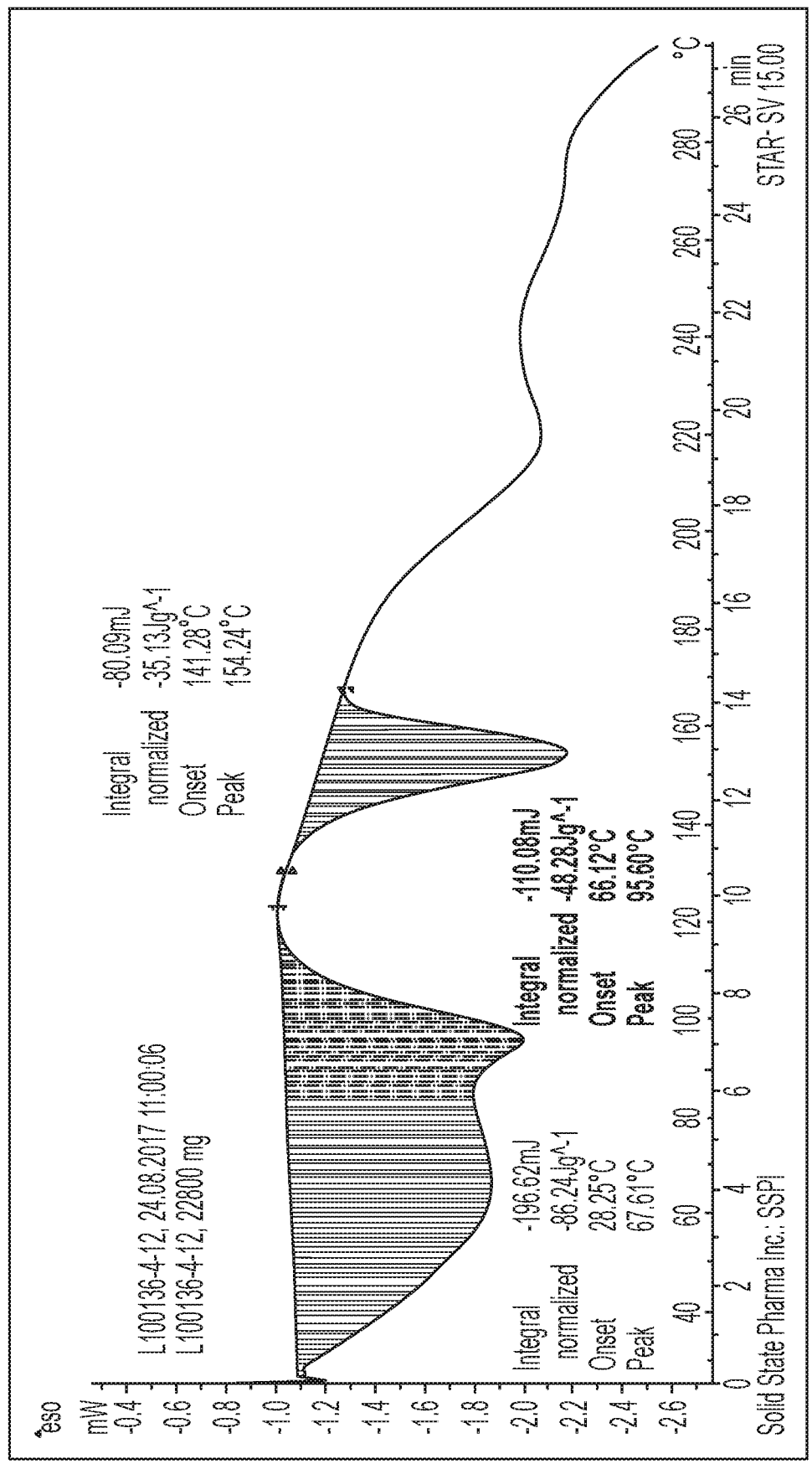
FIG. 3 depicts a DSC profile of crystalline Pattern A of bis-HCl salt of Compound (I).
Figure 4:
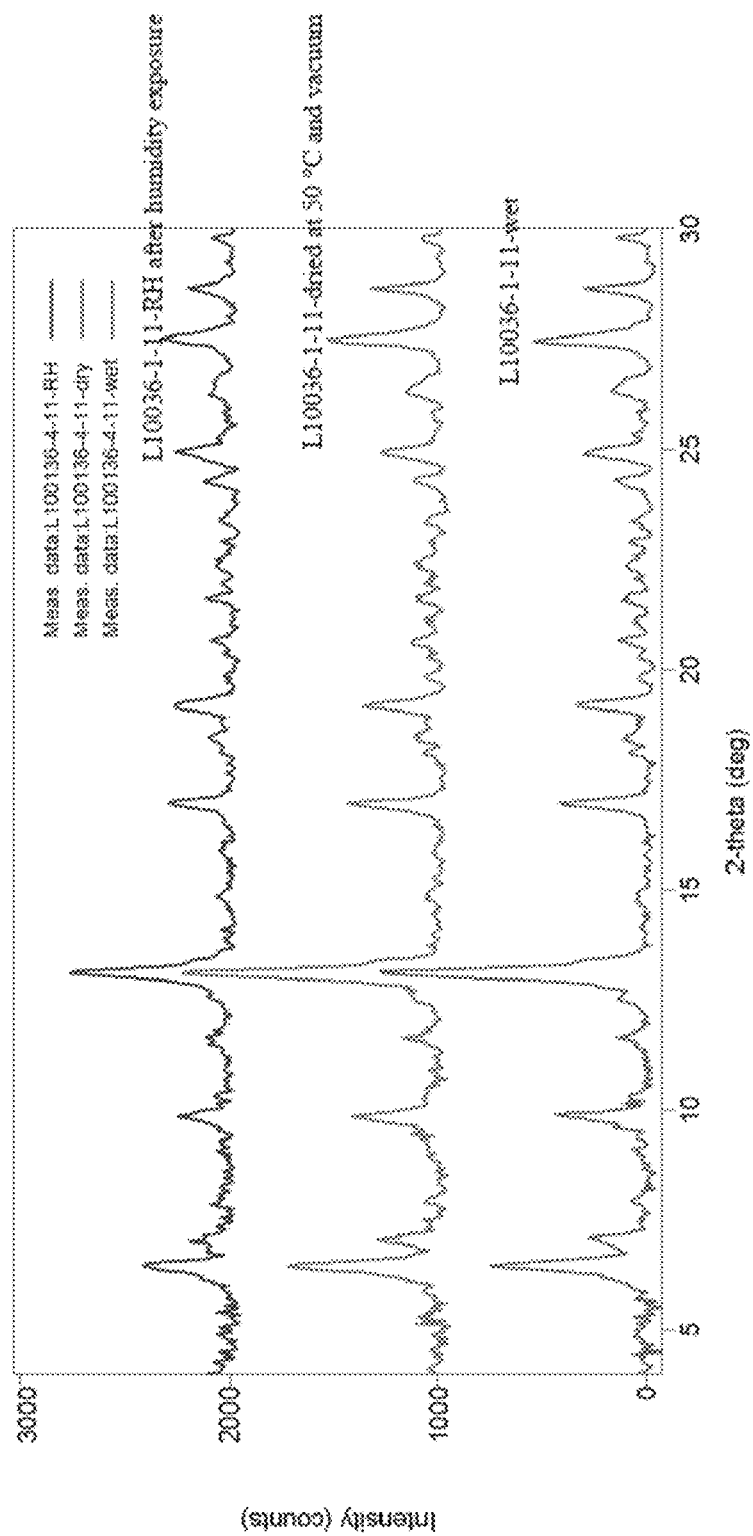
FIG. 4 depicts XRPD patterns of wet, dry, and humidity-exposed samples of the crystalline bis-HCl salt of Compound (I) of Pattern A.
Figure 5:
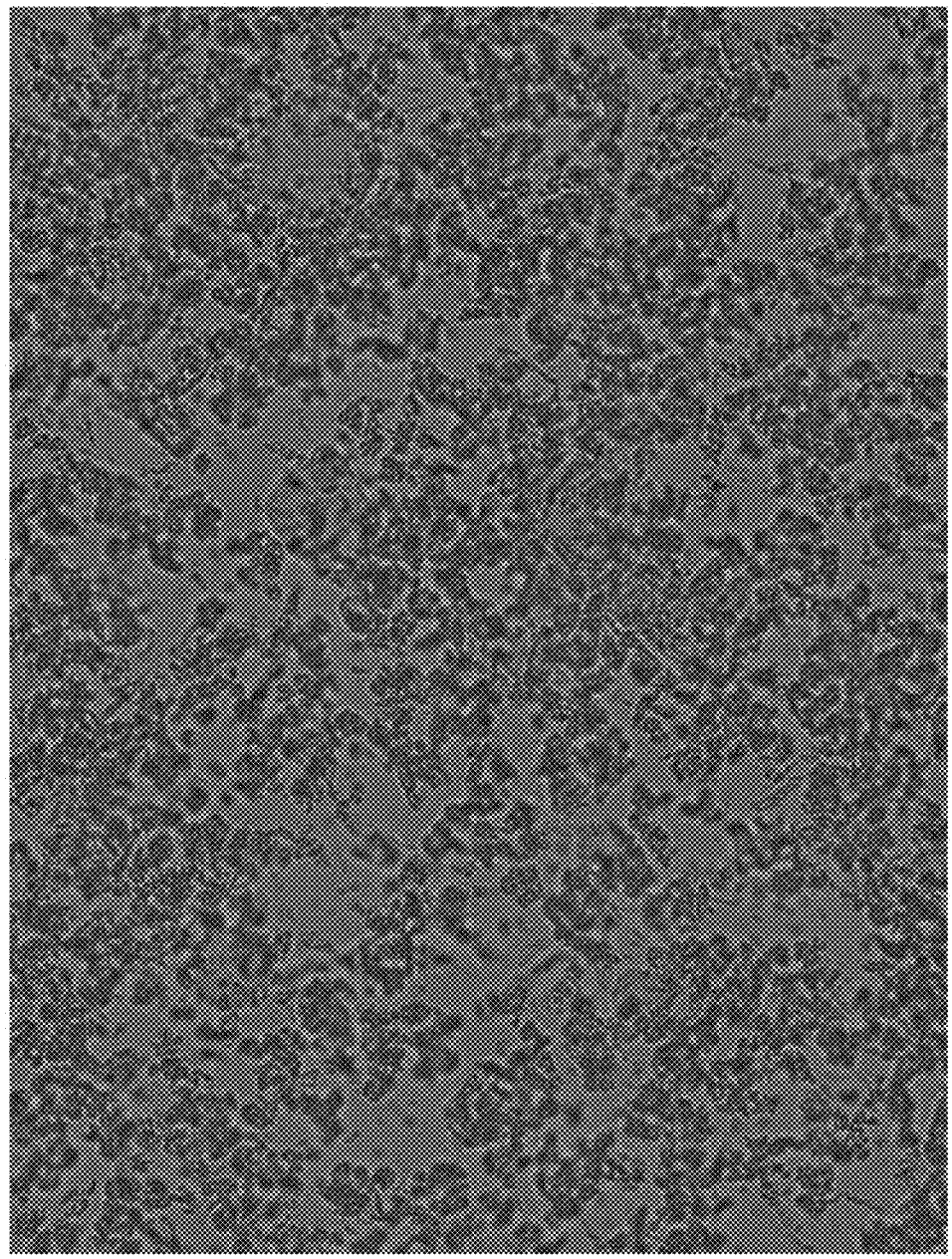
FIG. 5 depicts a microscopy image of the crystalline solid from experiment L100136-10-wet (one eq. NaOH in Water/NaCl (20%)).
Figure 6:
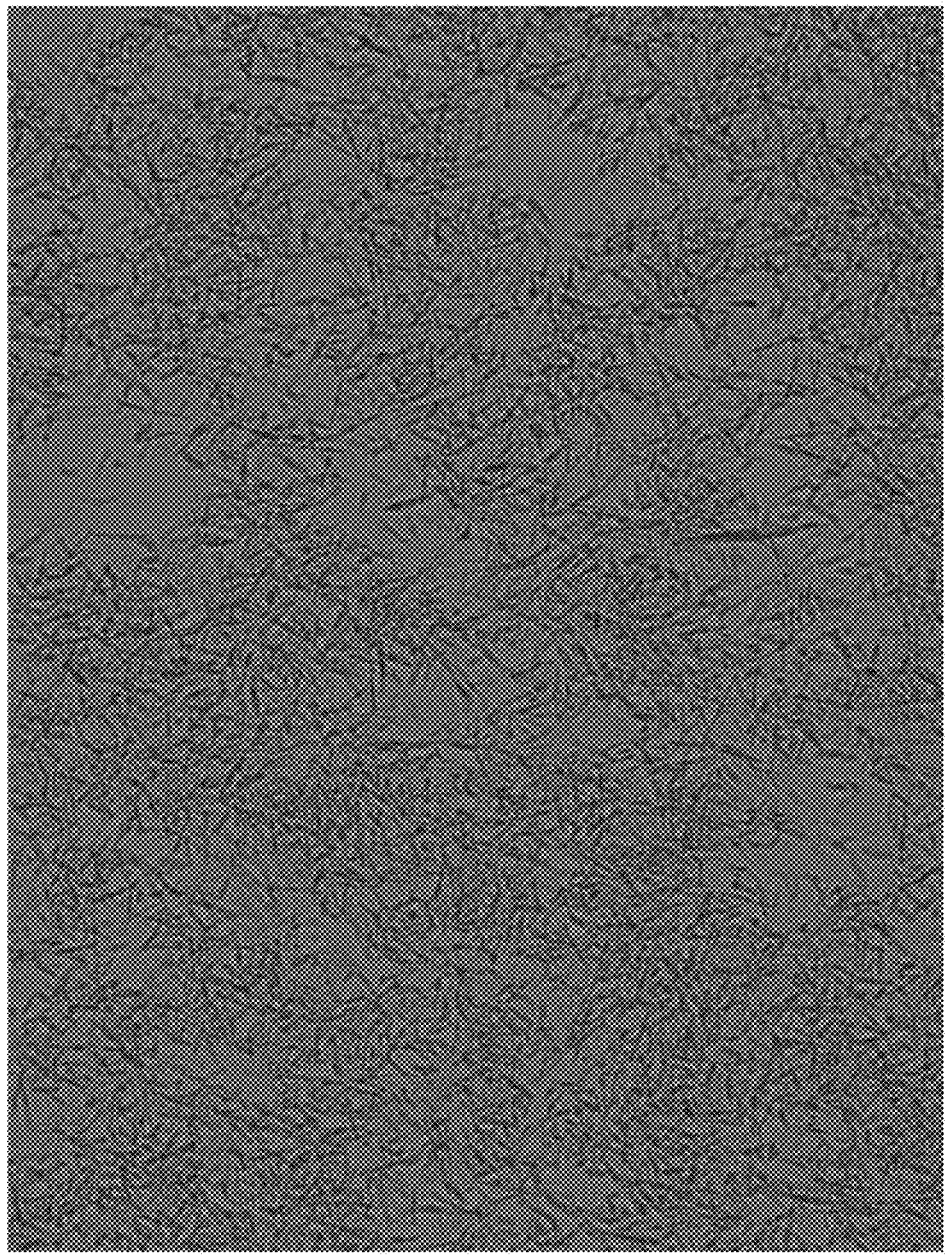
FIG. 6 depicts a microscopy image of the crystalline solid from L100136-11-wet (two eq. NaOH in Water/NaCl (20%)).
Figure 7:
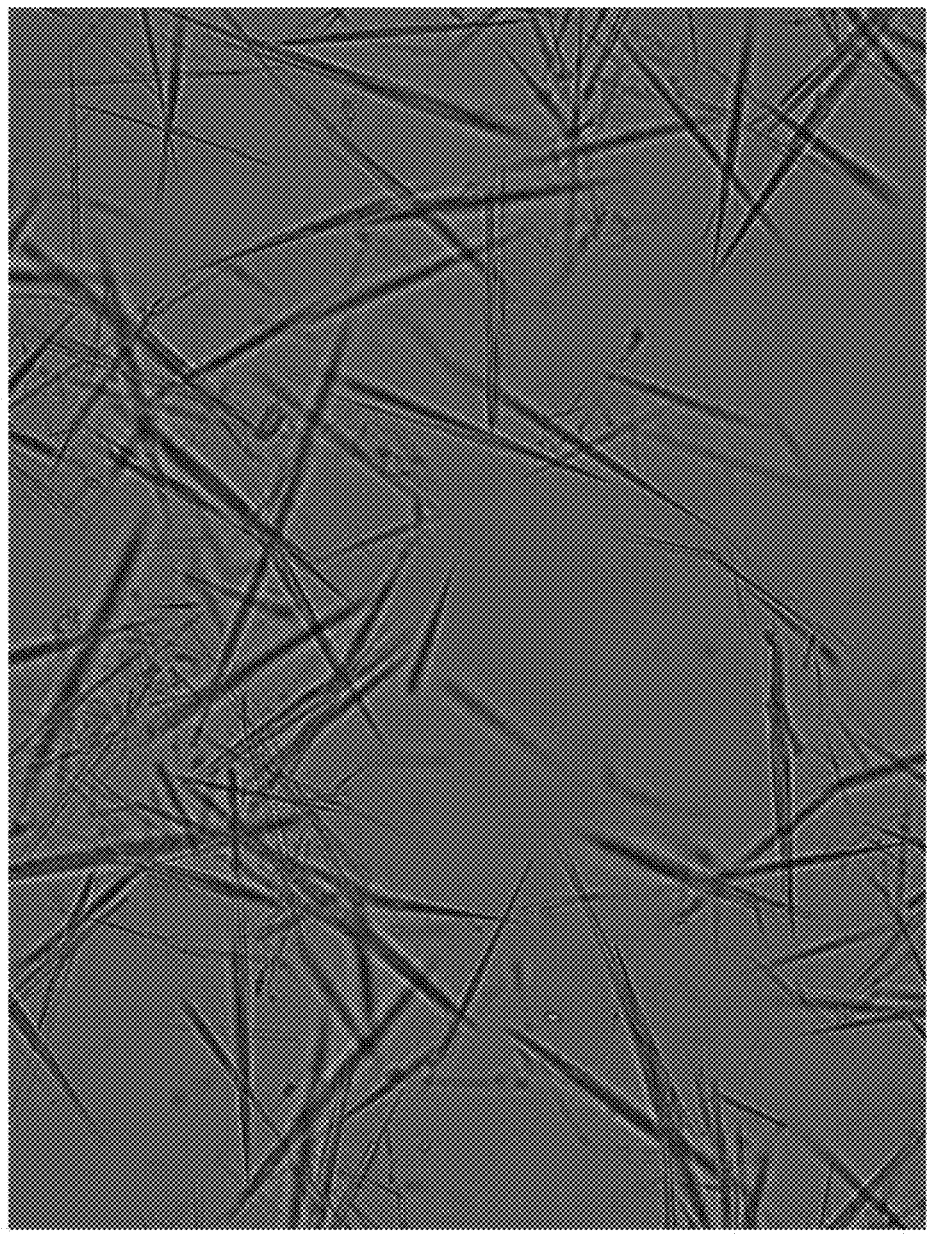
FIG. 7 depicts a microscopy image of the crystalline solid from L100136-12-wet (3 eq. NaOH in Water/NaCl (20%)).
Figure 8:
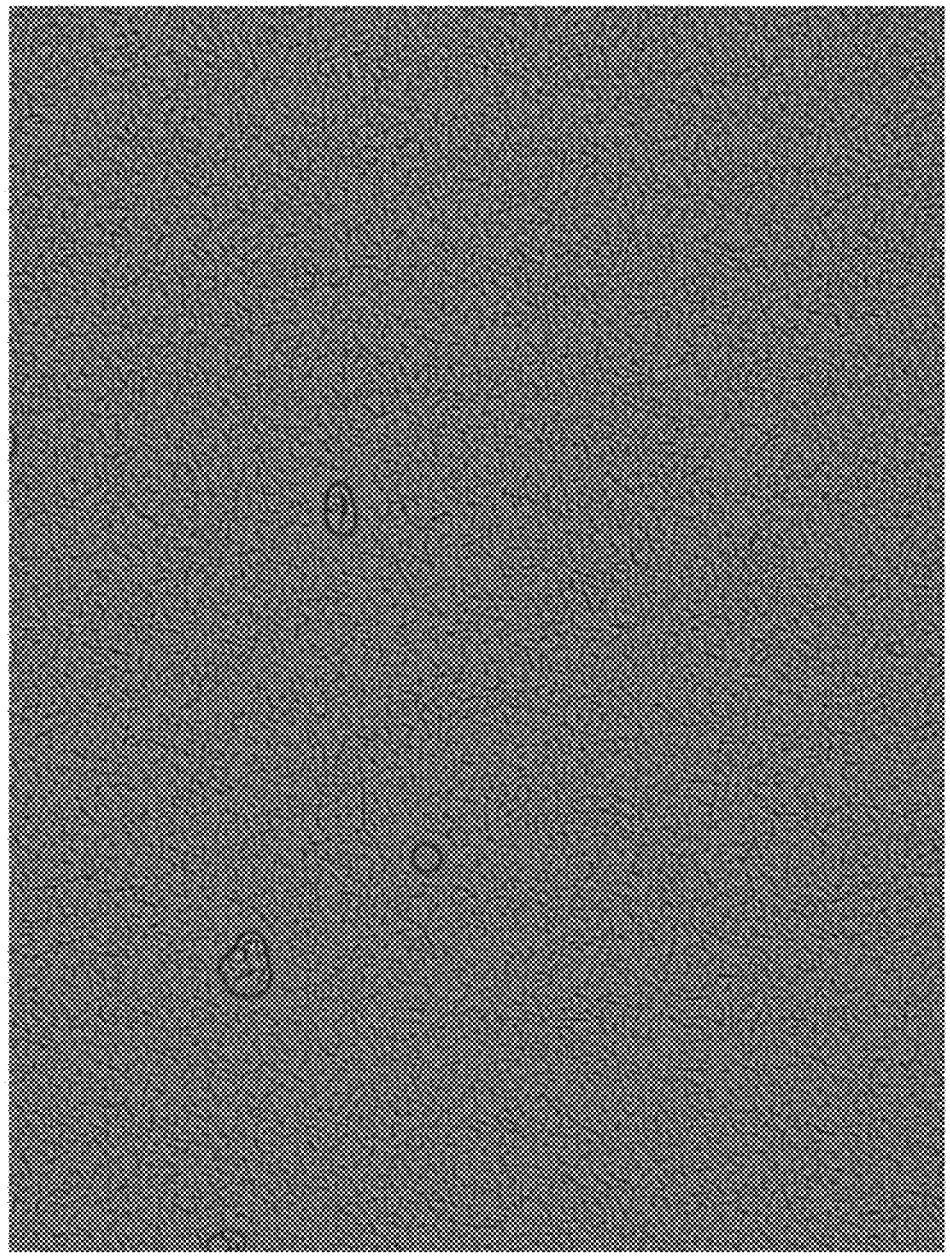
FIG. 8 depicts a microscopy image of the crystalline solid from experiment L100136-14-wet (two eq. NaOH in Water/NaCl (10%)).

In one aspect, the invention features a crystalline form of Compound (I) which has characteristic peaks in the powder X-ray diffraction (XRPD) pattern as shown in FIG. 3.

In another aspect, the invention features a crystalline form of Compound (I) which has characteristic peaks in the powder X-ray diffraction (XRPD) pattern at values of two theta (° 2θ) as shown in Table 10.

Figure 9:
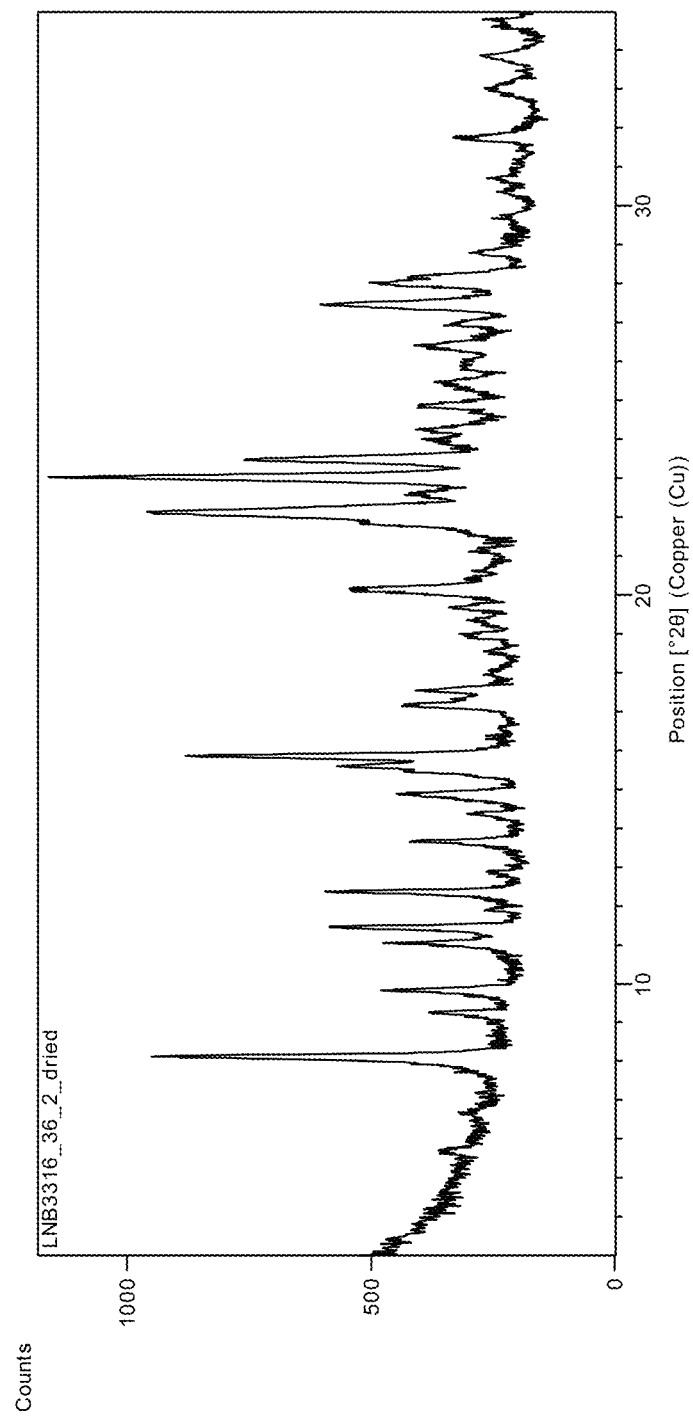
FIG. 9 is XRPD Pattern 1 of the crystalline tris-HCl salt of Compound (I).
Figure 10:
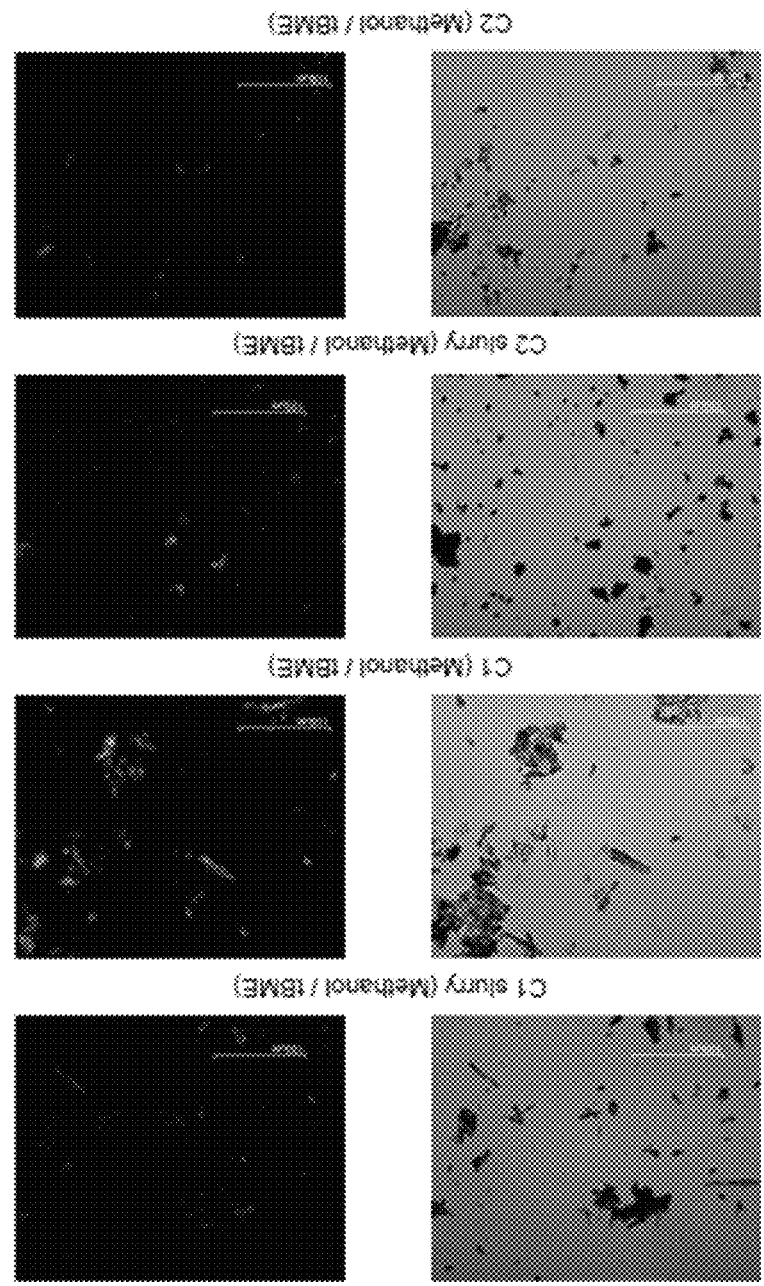
FIG. 10 depicts the PLM analysis of the crystalline tris-HCl salt of Compound (I).

The relative intensity, as well as the two theta value, of each peak in Table 10, as well as in FIG. 9, may change or shift under certain conditions, although the crystalline form is the same. One of ordinary skill in the art should be able to determine readily whether a given crystalline form is the same crystalline form as described in Table 10, as well as in FIG. 9, by comparing their XRPD data.

In yet another aspect, the invention features a crystalline form of a tris-hydrochloride salt of Compound (I) which has characteristic peaks in the powder X-ray diffraction (XRPD) pattern as shown in FIG. 9.

In yet another aspect, the invention features a crystalline form of a tris-hydrochloride salt of Compound (I) which has characteristic peaks in the powder X-ray diffraction (XRPD) pattern as shown in Table 10.

In another aspect, the invention features a crystalline form of a tris-hydrochloride salt of Compound (I) which has characteristic peaks in the powder X-ray diffraction (XRPD) pattern at values of two theta (° 2θ) of 8.1, 11.5, 15.6, 15.9, 22.1, 23.0, and 27.4.

In another aspect, the invention features a crystalline form of a tris-hydrochloride salt of Compound (I) which has characteristic peaks in the powder X-ray diffraction (XRPD) pattern at values of two theta (° 2θ) of 8.1, 9.8, 11.0, 11.5, 12.4, 14.9, 15.6, 15.9, 20.1, 21.8, 22.1, 23.0, 27.4, and 28.0.

The term "substantially pure" as used herein, refers to a crystalline polymorph that is greater than 90% pure, meaning that contains less than 10% of any other compound, including the corresponding amorphous compound or an alternative polymorph of the crystalline salt. Preferably, the crystalline polymorph is greater than 95% pure, or even greater than 98% pure.

In one embodiment, the present invention features a crystalline form of Compound (I) which has characteristic peaks in the powder X-ray diffraction (XRPD) pattern as shown in FIG. 2 and which is substantially pure. For example, the crystalline form can be at least 90% pure, preferably at least 95% pure, or more preferably at least 98%.

Methods of Making the Crystalline Salts

In certain embodiments, the invention relates to a method for the preparation of a crystalline salt of a compound having the structure of formula (I), comprising a) providing a freebase mixture of a compound of formula (I) in a first organic solvent; b) contacting the freebase mixture with a reagent solution comprising an acid and optionally a second organic solvent under conditions sufficient to form a mixture comprising a salt of the compound of formula (I); and c) crystallizing the salt of the compound of formula (I) from the mixture comprising a salt of the compound of formula (I).

In certain embodiments, the invention relates to a method for the preparation of a crystalline salt of a compound having the structure of formula (I), comprising a) providing a first salt mixture of a compound of formula (I) in a first organic solvent; b) contacting the first salt mixture with a reagent solution comprising an acid and optionally a second organic solvent under conditions sufficient to form a mixture comprising a second salt of the compound of formula (I); and c) crystallizing the second salt of the compound of formula (I) from the mixture comprising a second salt of the compound of formula (I).

In certain embodiments, the invention relates to a method for the preparation of a crystalline salt of a compound having the structure of formula (I), comprising a) providing a first mixture comprising a protected form of a compound of formula (I) in a first organic solvent; b) contacting the first mixture with a reagent solution comprising an acid and optionally a second organic solvent under conditions sufficient to deprotect the protected form of the compound of formula (I) and to form a mixture comprising a salt of the compound of formula (I); and c) crystallizing the salt of the compound of formula (I) from the mixture comprising a salt of the compound of formula (I).

In certain embodiments, the mixture comprising a salt of the compound of formula (I) formed in step b) is a solution. In certain embodiments, the mixture formed in step b) is a slurry or a suspension.

In certain embodiments, the mixture comprising the salt of the compound of formula (I) is a solution, and the step of crystallizing the salt from the mixture comprises bringing the solution to supersaturation to cause the salt of the compound of formula (I) to precipitate out of solution.

In certain embodiments, bringing the mixture comprising the salt of a compound of formula (I) to supersaturation comprises the slow addition of an anti-solvent, such as heptanes, hexanes, ethanol, or another polar or non-polar liquid miscible with the organic solvent, allowing the solution to cool (with or without seeding the solution), reducing the volume of the solution, or any combination thereof. In certain embodiments, bringing the mixture comprising the salt of a compound of formula (I) to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises isolating the salt crystals, e.g. by filtering the crystals, by decanting fluid from the crystals, or by any other suitable separation technique. In further embodiments, the preparation method further comprises washing the crystals.

In certain embodiments, the preparation method further comprises inducing crystallization. The method can also comprise the step of drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In certain embodiments, the freebase mixture of a compound of formula (I) in a first organic solvent is a slurry. In certain embodiments, the freebase mixtures of a compound of formula (I) in a first organic solvent is a solution.

In certain embodiments, the first organic solvent and the second organic solvent, if present, comprise acetone, anisole, methanol, 1-butanol, 2-butanone, iso-butanol, tert-butanol, sec-butanol, cyclopentyl methylester (CPME), benzotrifluoride (BTF), 1-propanol, 2-propanol (IPA), water, dichloromethane, anisole, acetonitrile, ethylene glycol, tert-butyl methyl ether (t-BME), DMSO, ethylene glycol, toluene, tetrahydrofuran (THF), heptane, acetonitrile, N,N-dimethylacetamide (DMA), dimethylformamide (DMF), dimethylsulfoxide (DMSO), 1,4-dioxane, 2-ethoxy ethanol, heptane, isopropyl acetate, methyl acetate, 2-methyl THF, methyl isobutyl ketone (MIBK), 1-propanol, ethanol, ethyl acetate, hexanes, methyl acetate, isopropyl acetate, methylethyl ketone, 1,4-dioxane, methyl cyclohexane, N-methyl-2-pyrrolidone (NMP), or any combination thereof.

In certain embodiments, the first organic solvent and the second organic solvent, if present, are the same. In alterative embodiments, the first organic solvent and the second organic solvent, if present, are different.

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the salt crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is ethanol.

In certain embodiments, washing the crystals comprises washing the crystalline compound of formula (I) with a solvent or a mixture of one or more solvents, which are described above. In certain embodiments, the solvent or mixture of solvents is cooled prior to washing.

Pharmaceutical Compositions

In certain embodiments, the present invention relates to pharmaceutical compositions comprising a crystalline compound or salt of a compound of formula (I) and one or more pharmaceutically acceptable excipients.

Exemplary pharmaceutically acceptable excipients are presented herein, and include, for example binders, disintegrating agents, lubricants, corrigents, solubilizing agents, suspension aids, emulsifying agents, coating agents, cyclodextrins, and/or buffers. The appropriate dosage of Compound (I) varies depending on the patient's symptoms, age and body weight of the patient, the nature and severity of the disorder to be treated or prevented, the route of administration and the form of the drug. Generally, a daily dosage of from 0.01 to 3000 mg of Compound (I) is recommended for an adult human patient, which may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

In certain embodiments, the individual to which the composition is administered is a mammal such as a human, or a non-human mammal. When administered to an animal, such as a human, the composition or the Compound (I)s preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is sterile and pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop, through ophthalmic mucous membrane administration or penetration of the corneal epithelium.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextran, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the compounds. These salts can be prepared in situ during the final isolation and purification of the compounds, or by separately reacting a purified Compound (I)n its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. Preparation of the crystalline salts is detailed in the Examples, below (See, for example, Berge et al. (1977) "Pharmaceutical Salts", J. Pharm. Sci. 66: 1-19.).

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound. These salts can likewise be prepared in situ during the final isolation and purification of the compound, or by separately reacting the purified Compound (I)n its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Other representative salts include the copper and iron salts. Representative organic amines useful for the formation of base addition salts include ethylamine, diethylamine, ethylenediamine, ethanolamine, diethanolamine, piperazine, and the like (see, for example, Berge et al., supra).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually or buccally); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896 (all of which are incorporated by reference).

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. Compositions or compounds may also be administered as a bolus, electuary or paste.

To prepare solid dosage forms for oral administration capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the compositions of the present invention can also include adjuvants such as wetting agents, lubricants, emulsifying and suspending agents such as sodium lauryl sulfate and magnesium stearate, or sweetening, flavoring, coloring, perfuming, preservative, or antioxidant agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively, or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, vaginal rings for sustained-release (e.g., polymeric vaginal rings) creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compounds described herein can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the present invention to the body. Such dosage forms can be made by dissolving or dispersing Compound (I) in the proper medium. Absorption enhancers can also be used to increase the flux of the compound across the skin. The rate of such flux can be controlled by either providing a rate controlling membrane or dispersing the Compound (I)n a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of all of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, intravitreal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, metacresol, benzoic acid and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous, intravitreal or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of metabolism or excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1 single or 2-4 divided doses. Each divided dose may contain the same or different compounds of the invention.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882).

In general, a suitable daily dose of an active compound used in the compositions and methods of the invention will be that amount of the compound that is the lowest dose effective to produce a therapeutic effect or the maximally tolerated dose. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second Compound (I)s administered while the previously administered therapeutic Compound (I)s still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn, Cu, Fe or other metal salts.

The pharmaceutically acceptable acid addition salts can also exist as various solvates, such as with water, methanol, ethanol, dimethylformamide, dichloromethane, acetonitrile, acetone, ethyl acetate, cyclopentyl methyl ether and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Materials and Methods for Examples 1-4

X-Ray Diffraction

Powder x-ray diffraction (XRPD) experiments were performed on a Rigaku MiniFlex 600 equipped with a Cu Kα radiation source (wavelength of x-rays 1.54 Å), and a scintillation detector. Samples were prepared on Si zero-return wafers. Scans were performed from 2θ 4 to 30 degrees over a step size of 0.05 over thirty minutes with cathode ray tube voltage and current 40 kV and 15 mA, respectively.

Differential Scanning Calorimetry (DSC)

Differential scanning calorimetry was performed on a Mettler Toledo TGA/DSC3+. A heating rate of 10° C./min was employed, and the scan was performed over a range of 30 to 300° C. A typical sample size of about 6-8 mg was used. A standalone DSC 3+ was also used to obtain thermograms of certain samples.

Example 1. Effect of pH in Organic Solvent

To assess precipitation four different equivalences of base (0.6, 1, 2 and 3) were added to solutions of MTP-131 tris-HCl in various solvent systems. The utilized solvents were IPA, ethanol, and methyl acetate. The additions and stirring of solutions were at room temperature. The bases were sodium hydroxide and ammonium hydroxide. Most of experiments resulted in an amorphous solid, a solution, or oiled/gummed.

TABLE 1

The effect of base, equivalencies, and solvents on formation of crystalline bis-HCl salt

| L100136-2- | Solid, mg | Solvent | Solvent, μL | Base solution | eq. | Observation | XRD |
|---|---|---|---|---|---|---|---|
| 1 | 98.1 | IPA | 981 | aq. NaOH | 0.6 | Gummed | |
| 2 | 97.7 | IPA | 977 | aq. NaOH | 1 | Gummed/oiled | |
| 3 | 95.3 | IPA | 953 | aq. NaOH | 1.5 | oiled | |
| 4 | 100.5 | IPA | 1005 | aq. NaOH | 2 | dissolved | |
| 5 | 101.3 | IPA | 1013 | NaOH/EtOH | 0.6 | Slurry | Amorphous |
| 6 | 103.7 | IPA | 1037 | NaOH/EtOH | 1 | Slurry | Amorphous |
| 7 | 112.4 | IPA | 1124 | NaOH/EtOH | 1.5 | Slurry | Amorphous |
| 8 | 91.6 | IPA | 916 | NaOH/EtOH | 2 | Slurry-somewhat sticky | Amorphous |
| 9 | 94.8 | IPA | 948 | Am. Hydroxide | 0.6 | Slurry | Amorphous |
| 10 | 103.6 | IPA | 1036 | Am. Hydroxide | 1 | Slurry | Amorphous |
| 11 | 103.3 | IPA | 1033 | Am. Hydroxide | 1.5 | Slurry-Gum | |
| 12 | 101.4 | IPA | 1014 | Am. Hydroxide | 2 | Gum | |
| 13 | 99.5 | EtOH | 995 | aq. NaOH | 0.6 | oiled | |
| 14 | 94.2 | EtOH | 942 | aq. NaOH | 1 | oiled | |
| 15 | 95.2 | EtOH | 952 | aq. NaOH | 1.5 | oiled | |
| 16 | 101.5 | EtOH | 1015 | aq. NaOH | 2 | dissolved | |
| 17 | 96.7 | EtOH | 967 | NaOH/EtOH | 0.6 | Gum-clear | |
| 18 | 97.1 | EtOH | 971 | NaOH/EtOH | 1 | Gum-cloudy | |
| 19 | 104.1 | EtOH | 1041 | NaOH/EtOH | 1.5 | Cloudy | |
| 20 | 107.2 | EtOH | 1072 | NaOH/EtOH | 2 | Cloudy | |
| 21 | 99.9 | EtOH | 999 | Am. Hydroxide | 0.6 | Gum-clear | |
| 22 | 92.1 | EtOH | 921 | Am. Hydroxide | 1 | Gum-clear | |
| 23 | 106.3 | EtOH | 1063 | Am. Hydroxide | 1.5 | Gum-clear | |
| 24 | 106.1 | EtOH | 1061 | Am. Hydroxide | 2 | dissolved | |
| 25 | 100.7 | MeOAc | 1007 | aq. NaOH | 0.6 | Gum/oil | |
| 26 | 96.1 | MeOAc | 961 | aq. NaOH | 1 | oiled | |
| 27 | 93.8 | MeOAc | 938 | aq. NaOH | 1.5 | oiled | |
| 28 | 95.8 | MeOAc | 958 | aq. NaOH | 2 | oiled | |
| 29 | 103.5 | MeOAc | 1035 | NaOH/EtOH | 0.6 | Slurry | Amorphous |
| 30 | 98.8 | MeOAc | 988 | NaOH/EtOH | 1 | Slurry | Amorphous |
| 31 | 98.3 | MeOAc | 983 | NaOH/EtOH | 1.5 | Gum-cloudy | |
| 32 | 96.5 | MeOAc | 965 | NaOH/EtOH | 2 | Gum-clear | |
| 33 | 94.5 | MeOAc | 945 | Am. Hydroxide | 0.6 | Slurry | Amorphous |
| 34 | 96.3 | MeOAc | 963 | Am. Hydroxide | 1 | Slurry | Amorphous |
| 35 | 97.4 | MeOAc | 974 | Am. Hydroxide | 1.5 | Slurry-Gum | Amorphous |
| 36 | 100.4 | MeOAc | 1004 | Am. Hydroxide | 2 | Gum | |

Example 2. Effect of Drying and Humidity Exposure on New Crystalline Solid

The crystalline solid was dried at 50 C under vacuum overnight, and analyzed by XRPD. No changes were observed in the XRPD pattern showing that the solid stable upon drying. Furthermore, the dry solid was exposed to about 95% relative humidity at room temperature for 24 hours followed by XRPD analysis. The solid physically kept its integrity. The XRPD also remained unchanged. It should be noted that 3-HCl salt of MTP-131 deliquesces at more than 70% relative humidity.

Example 3. Generation of Pattern a in Pure Water Through Seeding

The solubility of the crystalline solid was assessed qualitatively in water. It was about 60 mg/mL at room temperature. One may generate the new crystalline solid in pure water by seeding a supersaturated solution. The following procedure was performed:
1. 101 mg of MTP-131 tri-HCl were added to a 4 mL vial;
2. 500 µL water were added to the vial, which dissolved the solid;
3. 2 eq. of sodium hydroxide (22.5 µL of 35% aq. NaOH) were added;
4. the solution remained clear;
5. Pattern A seeds from lot L100136-4-14 were added; seeds were retained;
6. the solution became hazy solution within minutes and formed a slurry within 15 minutes;
7. the solution was stirred overnight, resulting in a thick slurry;
8. the slurry was filtered and washed with 200 µL water;
9. drying at 50° C. under vacuum was performed. The XRPD was consistent with Pattern A.

Example 4. Crystalline Bis-HCl Salt of MTP-131—XRPD Peak List

TABLE 2

| 2θ (°) | d spacing (A°) | Height (cps) | Relative intensity (%) |
|---|---|---|---|
| 6.40 | 13.79726 | 1343 | 28 |
| 6.98 | 12.65711 | 406 | 9 |
| 7.88 | 11.20719 | 160 | 3 |
| 9.05 | 9.76484 | 112 | 2 |
| 9.84 | 8.97904 | 1550 | 33 |
| 10.18 | 8.67918 | 186 | 4 |
| 11.65 | 7.58843 | 340 | 7 |
| 13.06 | 6.77213 | 4732 | 100 |
| 16.88 | 5.24746 | 715 | 15 |
| 19.09 | 4.64608 | 790 | 17 |
| 20.61 | 4.30611 | 289 | 6 |
| 24.21 | 3.67305 | 113 | 2 |
| 24.84 | 3.58126 | 433 | 9 |
| 26.33 | 3.38163 | 298 | 6 |
| 27.44 | 3.24777 | 327 | 7 |
| 28.59 | 3.11934 | 158 | 3 |
| 29.73 | 3.00251 | 480 | 10 |

Materials and Methods for Examples 5-11

X-Ray Diffraction

Powder x-ray diffraction (XRPD) experiments were performed on PANalytical X'Pert Pro X-ray Diffractometer, scanning the samples between 3 and 35° 2θ. Material was loaded into a 96-well plate with mylar film as the base. The samples were then loaded into the plate holder of a PANalytical X'Pert Pro X-ray Diffractometer running in transmission mode and analyzed, using the following experimental conditions:

Raw Data Origin: XRD measurement (*.XRDML)
Scan Axis: Gonio
Start Position [° 2θ]: 3.0066
End Position [° 2θ]: 34.9866
Step Size [° 2θ]: 0.0130
Scan Step Time [s]: 18.8700
Scan Type: Continuous
PSD Mode: Scanning
PSD Length [° 2θ]: 3.35
Offset [° 2θ]: 0.0000
Divergence Slit Type: Fixed
Divergence Slit Size [°]: 1.0000
Specimen Length [mm]: 10.00
Measurement Temperature [° C.]: 25.00
Anode Material: Cu
K-Alpha1 [Å]: 1.54060
K-Alpha2 [Å]: 1.54443
K-Beta [Å]: 1.39225
K-A2/K-A1 Ratio: 0.50000
Generator Settings: 40 mA, 40 kV
Diffractometer Type: 0000000011154173
Diffractometer Number: 0
Goniometer Radius [mm]: 240.00
Dist. Focus-Diverg. Slit [mm]: 91.00
Incident Beam Monochromator: No
Spinning: No Polarized Light Microscopy (PLM)

The presence of birefringence was determined using an Olympus BX50 polarizing microscope, equipped with a Motic camera and image capture software (Motic Images Plus 2.0). All images were recorded using the 20× objective, unless otherwise stated.

Thermogravimetric/Differential Thermal Analysis (TG/DTA)

Approximately 5 mg of material was weighed into an open aluminium pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 $cm^3$/min.

Differential Scanning Calorimetry (DSC)

Approximately 5 mg of material was weighed into an aluminium DSC pan and sealed nonhermetically with a pierced aluminium lid. The sample pan was then loaded into a Seiko DSC6200 (equipped with a cooler) and held at 20° C. Once a stable heat-flow response was obtained, the sample and reference were heated to ca. 270° C. at a scan rate of 10° C./min and the resulting heat flow response monitored. Nitrogen was used as the purge gas, at a flow rate of 50 cm3/min.

Karl Fischer Coulometric Titration (KF)

Approximately 10 or 100 mg of solid material was accurately weighed into a vial. The solid was then dissolved in ca. 1 mL or 5 mL of pre-titrated Hydranal solution, sonicating for ca. 5-10 min. The solution was manually introduced into the titration cell of a Mettler Toledo C30 Compact Titrator and the weight of the solid entered on the instrument.

1H Nuclear Magnetic Resonance Spectroscopy (1H NMR)

1H-NMR spectroscopic experiments were performed on a Bruker AV500 (frequency: 500 MHz). Experiments were performed in d6-dimethylsulfoxide and each sample was prepared to ca. 10 mM concentration.

Gravimetric Vapour Sorption (GVS)

Approximately 15 mg of sample was placed into a mesh vapour sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion). After completion of the sorption cycle, the sample was dried using the same procedure to 0% RH, then subjected to a second ramping profile from 0-90% relative humidity. After completion of the second sorption cycle, the sample was dried using the same procedure to 0% RH, and finally taken back to the starting point of 40% RH. The weight change during the sorption/desorption cycles were plotted, allowing for the hygroscopic nature of the sample to be determined.

High Performance Liquid Chromatography-Ultraviolet Detection (HPLC-UV)

Column: Aeris Peptide C18 3.6 μm 250×4.6 mm column
Mobile Phase A: 0.05% TFA in deionized water
Mobile Phase B: 0.05% TFA in acetonitrile
Diluent: Water:Acetonitrile (90:10 v/v)
Flow Rate: 1.0 mL/min
Runtime: 32 minutes
Column Temperature: 30° C.
Autosampler Temperature: 5° C.
Injection Volume: 30 μL
Detection: 220 nm
Sample Concentration: 0.5 mg/mL Gradient program:

| Time/min | Solvent B (%) |
|---|---|
| 0.00 | 5 |
| 15.00 | 25 |
| 20.00 | 50 |
| 25.00 | 90 |
| 27.00 | 90 |
| 27.10 | 5 |
| 32.00 | 5 |

Ion Chromatography (IC)

Column: Thermo Acclaim P2 50×2.1 mm, 3 μm
Mobile Phase A: DI H2O or H2O:MeCN (10:90 v/v)
Mobile Phase B: 100 mM, pH 3.65 Ammonium Formate buffer
Diluent: DI water
Flow Rate: 0.3 mL/min
Runtime: 22.5 minutes
Column Temperature: 30° C.
Autosampler Temperature Ambient
Injection Volume: 5 μL
Sample Concentration: 0.1 mg/mL in water
Detection: CAD, 100 pA, Low filter Gradient Program:

| Time/min | Solvent B (%) |
|---|---|
| 0.0 | 10 |
| 1 | 10 |
| 11.0 | 90 |
| 17.5 | 90 |
| 17.51 | 10 |
| 22.5 | 10 |

Example 5. Approximate Solubility of MTP-131 HCl

The approximate solubility values of MTP-131 HCl, Batch: 04-PD-040-2 in the selected solvent systems (Table 3) were estimated by a solvent addition technique. The solubility screen was carried out as follows:

Approximately 20 mg of MTP-131 HCl, Batch: 04-PD-040-2 was weighed out into each vial.

Each solvent/solvent mixture was added to the appropriate vial in 5 volume aliquots (100 μL).

In between additions, the sample was stirred at 50° C. (35° C. for DCM).

If 2000 μl of solvent was added without dissolution of the material, solubility was calculated to be below this point.

XRPD analysis of residual solids was carried out where solubility was <10 mg/mL.

Residual solids from water mixtures were fully dissolved by addition of further water, while remaining residual solids were fully dissolved by addition of methanol (Table 4).

Anti-solvent was added to the solutions (initial solvent or tBME) which were stirred at 5° C. to encourage crystallization (Table 4).

Any solids were isolated and analyzed by XRPD.

TABLE 3

Solvent Systems Selected for Solubility Screen

| Solvent | ICH Class | Solvent Mixture | ICH Class |
|---|---|---|---|
| Acetone | 3 | Acetone:Water (95:5 v/v) | 3 |
| Dichloromethane | 2 | Acetonitrile:Water (95:5 v/v) | 2 |
| Ethanol | 3 | Acetonitrile:Water (99:1 v/v) | 2 |
| Methanol | 2 | Ethanol:Water (95:5 v/v) | 3 |
| 2-Propanol | 3 | Methanol:Water (95:5 v/v) | 2 |
| Trifluoroethanol | Not classified | 2-Propanol:Water (95:5 v/v) | 3 |
| | | 2-Propanol:Water (99:1 v/v) | 3 |
| | | THF:Water (95:5% v/v) | 2 |
| | | THF:Water (99:1 v/v) | 2 |
| | | Acetonitrile:DMSO (85:15 v/v) | 2 |
| | | DCM:DMSO (85:15 v/v) | 2 |
| | | Ethanol:DMSO (95:5% v/v) | 3 |

TABLE 4

Experimental Details for Solubility Screen ASA Experiments

| | | | Initial Solvent | | Additional Solvent | | Further Solvent | |
|---|---|---|---|---|---|---|---|---|
| Exp. | Initial Solvent System | | Vol./mL | Solvent | Vol./mL | Solvent | Vol./mL | |
| 1 | Acetone | | 2.4 | MeOH | 0.7 | tBME | 0.4 | |
| 2 | Ethanol | | 2.0 | tBME | 1.0 | | | |
| 3 | Methanol | | 0.2 | tBME | 0.4 | | | |
| 4 | 2-Propanol | | 2.6 | MeOH | 0.4 | | | |
| 5 | Dichloromethane | | 2.0 | MeOH | 0.5 | tBME | 0.8 | |
| 6 | Acetone:Water (95:5 v/v) | | 2.0 | H$_2$O, Acetone | 0.175, 0.1 | tBME, MeOH | 2.0, 0.4 | |
| 7 | Ethanol:Water (95:5 v/v) | | 0.3 | tBME | 0.2 | MeOH | 0.1 | |
| 8 | Methanol:Water (95:5 v/v) | | 0.1 | tBME | 0.2 | MeOH | 0.1 | |
| 9 | 2-Propanol:Water (95:5 v/v) | | 2.0 | Water | 0.2 | tBME, MeOH | 2.0, 1.0 | |
| 10 | Acetonitrile:Water (95:5 v/v) | | 2.0 | H$_2$O, MeCN | 0.125, 0.15 | tBME, MeOH | 2.0, 0.5 | |
| 11 | THF:Water (95:5% v/v) | | 2.0 | H$_2$O, THF | 0.125, 0.25 | tBME, MeOH | 2.0, 1.15 | |
| 12 | Ethanol:DMSO (95:5% v/v) | | 0.6 | EtOH | 0.6 | tBME | 0.1 | |
| 13 | 2-Propanol:Water (99:1 v/v) | | 2.0 | MeOH | 0.6 | tBME | 0.5 | |
| 14 | Acetonitrile:Water (99:1 v/v) | | 2.0 | MeOH | 0.7 | tBME | 0.4 | |
| 15 | THF:Water (99:1 v/v) | | 2.0 | MeOH | 0.6 | tBME | 0.4 | |
| 16 | Acetonitrile:DMSO (85:15 v/v) | | 2.0 | MeOH | 0.4 | | | |
| 17 | DCM:DMSO (85:15 v/v) | | 2.0 | MeOH | 0.1 | tBME | 0.6 | |
| 18 | Trifluoroethanol | | 2.0 | tBME | 0.3 | | | |

Example 6. Small-Scale Crystallization Screening

Small-scale crystallization trials using MTP-131 HCl, were carried out using the following procedures:

Maturation/Temperature Cycling Crystallizations:
- Approximately 50 mg of material (MTP-131 HCl) weighed into 1.5 mL screw-top vials.
- 500 or 250 µL of required solvent (ethanol, methanol, trifluoroethanol, dichloromethane, acetonitrile, THF or 2-propanol) added.
- Vials stirred at elevated temperature (40° C.) for ca. 0.5 h.
- Aliquots (100 µL) of additional solvent (MeOH, DMSO, DMF or H2O) added until material fully dissolved. If initial solvent resulted in dissolution, aliquots of anti-solvent (tBME, IPA, MIBK/IPA) added.
- Stirred at 40° C. for 1 h after complete dissolution then cooled to 35° C. and temperature cycling started (between 35-5° C., 2 h ramp/cool, 2 h hold at each temperature).
- After temperature cycling for ca. 16 h, experiments checked. Solids isolated by centrifugation and analyzed by XRPD.
- Solutions had further anti-solvent added (tBME or initial solvent) and temperature cycling continued.
- Volumes detailed in Table 5 refer to the total amount of that solvent used. Additional solvent was used to redissolve any amorphous solid or gums which formed, while further anti-solvent was added if no solids obtained.
- Water mixtures which separated due to partitioning of the material into one of the layers were homogenized through the addition of aliquots (100 µL) of 2-propanol.
- Crystalline material was isolated through centrifugation and dried under vacuum at 30° C. for ca. 24 h before being characterized by XRPD, PLM and HPLC.

Cooling Crystallizations:
- ca. 50 mg of MTP-131 HCl was weighed out into 1.5 mL screw-top vials.
- 250 µL of required solvent added (ethanol, methanol, trifluoroethanol, acetonitrile, THF or 2-propanol).
- Stirred at 50° C. as aliquots (100 µL) of additional solvent (MeOH, DMSO or H2O) added until material fully dissolved.
- If initial solvent resulted in dissolution, aliquots (100 µL) of anti-solvent (tBME, IPA, EtOAc) added at 50° C.
- Stirred at 50° C. for 4.5 h after complete dissolution then cooled to 5° C. over 7.5 h (0.1° C./min) before holding at 5° C.
- After stirring at 5° C. for ca. 12 h, experiments checked. Solids isolated by centrifugation and analyzed by XRPD.
- Solutions had further anti-solvent (tBME or initial solvent) added at 50° C. and cooling repeated (4×50-5° C. cools carried out, overall).
- Volumes detailed in Table 6 refer to the total amount of that solvent used. Additional solvent was used to redissolve any amorphous solid or gums which formed, while further anti-solvent was added if no solids obtained.
- Water mixtures which separated due to partitioning of the material into one of the layers, were homogenized through the addition of aliquots (100 µL) of 2-propanol.
- Crystalline material was isolated through centrifugation and dried under vacuum at 30° C. for ca. 24 h before being characterized by XRPD, PLM and HPLC.

Evaporation Crystallizations:
- The slurries from the solubility/ASA experiments (see Section 5.2 and Table 2) were redissolved through addition of 100 µL aliquots of methanol or water, with addition continuing until material fully dissolved.
- Solutions were left uncapped to evaporate at ambient temperature (ca. 20° C.) for 1 week.
- Solid material was analyzed by XRPD.

TABLE 5

Experimental Details for Small-Scale Temperature Cycling Crystallization Trials

| | Initial | Initial Solvent | | Additional Solvents | |
|---|---|---|---|---|---|
| Cryst$^n$ | Conc$^n$/ mg/mL | Solvent System | Vol./ mL | Solvent | Vol./ mL |
| 1 | 100 | Ethanol | 1.0 | MeOH | 0.3 |
| 2 | 100 | Methanol | 0.5 | tBME | 0.3 |
| 3 | 100 | Trifluoroethanol | 1.0 | MeOH | 0.3 |
| 4 | 100 | Dichloromethane | 1.0 | MeOH | 0.5 |

TABLE 5-continued

Experimental Details for Small-Scale Temperature Cycling Crystallization Trials

| Cryst$^n$ | Initial Conc$^n$/ mg/mL | Initial Solvent Solvent System | Vol./ mL | Additional Solvents Solvent | Vol./ mL |
|---|---|---|---|---|---|
| 5  | 100 | Acetonitrile     | 0.65 | MeOH      | 0.4 |
| 6  | 100 | Tetrahydrofuran  | 0.65 | MeOH      | 0.4 |
| 7  | 100 | 2-Propanol       | 0.9  | MeOH      | 0.7 |
| 8  | 100 | Ethanol          | 1.0  | DMSO      | 0.2 |
| 9  | 100 | Methanol         | 0.5  | IPA       | 0.6 |
| 10 | 100 | Trifluoroethanol | 0.8  | DMSO      | 0.3 |
| 11 | 100 | Dichloromethane  | 0.8  | DMSO      | 0.4 |
| 12 | 100 | Acetonitrile     | 0.75 | DMSO      | 0.4 |
| 13 | 100 | Tetrahydrofuran  | 0.75 | DMSO      | 0.5 |
| 14 | 100 | 2-Propanol       | 0.9  | DMSO      | 0.3 |
| 15 | 200 | Ethanol          | 0.85 | $H_2O$    | 0.1 |
| 16 | 200 | Water            | 0.25 | MIBK, IPA | 0.7, 0.6 |
| 17 | 200 | Trifluoroethanol | 0.85 | $H_2O$    | 0.1 |
| 18 | 200 | Dichloromethane  | 0.55 | DMF       | 0.5 |
| 19 | 200 | Acetonitrile     | 0.5  | $H_2O$, IPA | 0.05, 0.2 |
| 20 | 200 | Tetrahydrofuran  | 0.5  | $H_2O$, IPA | 0.05, 0.3 |
| 21 | 200 | 2-Propanol       | 0.65 | $H_2O$    | 0.1 |

TABLE 6

Experimental Details for Small-Scale Cooling Crystallization Trials

| Cryst$^n$ | Initial Conc$^n$/ mg/mL | Initial Solvent Solvent System | Vol./mL | Additional Solvents Solvent | Vol./mL |
|---|---|---|---|---|---|
| 1  | 200 | Ethanol          | 0.95  | MeOH         | 0.2 |
| 2  | 200 | Methanol         | 0.35  | tBME         | 0.2 |
| 3  | 200 | Trifluoroethanol | 1.05  | MeOH, tBME   | 0.5, 0.2 |
| 4  | 200 | Acetonitrile     | 0.4   | MeOH         | 0.35 |
| 5  | 200 | Tetrahydrofuran  | 0.4   | MeOH         | 0.35 |
| 6  | 200 | 2-Propanol       | 0.5   | MeOH         | 0.4 |
| 7  | 200 | Ethanol          | 1.05  | DMSO, tBME   | 0.2, 0.1 |
| 8  | 200 | Methanol         | 0.275 | IPA          | 0.25 |
| 9  | 200 | Trifluoroethanol | 0.95  | DMSO         | 0.25 |
| 10 | 200 | Acetonitrile     | 0.65  | DMSO, tBME   | 0.3, 0.1 |
| 11 | 200 | Tetrahydrofuran  | 0.65  | DMSO, tBME   | 0.3, 0.1 |
| 12 | 200 | 2-Propanol       | 0.85  | DMSO, tBME   | 0.2, 0.1 |
| 13 | 200 | Ethanol          | 1.15  | $H_2O$, tBME | 0.1, 0.1 |
| 14 | 200 | Methanol         | 0.25  | EtOAc, $H_2O$ | 0.2, 0.02 |
| 15 | 200 | Trifluoroethanol | 1.05  | $H_2O$, tBME | 0.1, 0.1 |
| 16 | 200 | Acetonitrile     | 0.85  | $H_2O$, tBME | 0.2, 0.1 |
| 17 | 200 | Tetrahydrofuran  | 0.75  | $H_2O$, IPA, tBME | 0.15, 0.1, 0.1 |
| 18 | 200 | 2-Propanol       | 1.05  | $H_2O$, tBME | 0.1, 0.1 |
| 19 | 333 | Methanol         | 0.35  | tBME         | 0.2 |
| 20 | 500 | Water            | 0.1   |              |     |

Example 6. Crystallization Scale-Up

MTP-131 HCl was re-crystallized using methanol and tBME. The following procedures were used:

Procedure 1:
Approximately 200 mg of MTP-131 HCl were weighed into 20 mL scintillation vial and dissolved in 1.4 mL of methanol at 50° C. with stirring.
Aliquots (100 µL) of tBME added slowly at 50° C. Crystallization began after 1.5 h (600 µL of tBME added).
Sample isolated by centrifugation and analyzed by XRPD.
Additional methanol added to redissolve solid (1.7 mL). Further aliquots (100 µL) of tBME added to encourage crystallization (2.0 mL in total).
Cooled from 50° C. to 5° C. at 0.1° C./min, held at 5° C. for ca. 16 h.
Sample isolated by centrifugation and analyzed by XRPD.
Heated to 50° C., added more methanol (so ratio 1.75:1 v/v), repeated cool.
Small amount of solid only. Sample isolated by centrifugation and analyzed by XRPD.
Additional methanol and tBME added, cooling repeated as required.
Solid isolated by centrifugation, washed with tBME (2.0 mL) and dried under vacuum for ca. 21 h at 35-40° C.
Dried material analyzed by XRPD, PLM and HPLC.

Procedure 2:
Approximately 200 mg of MTP-131 weighed into 20 mL scintillation vial.
Aliquots (250 µL) of MeOH:tBME 1.75:1 v/v added slowly at 50° C., with stirring. Full dissolution after 2.25 mL added.
After 0.75 h, crystallization occurred at 50° C. Sample isolated by centrifugation and analyzed by XRPD.
Aliquots of methanol (200 µL) added to redissolve solid (1.2 mL required).
Cooled from 50° C. to 5° C. at 0.1° C./min, held at 5° C. for ca. 16 h.
Small amount of solid only. Sample isolated by centrifugation and analyzed by XRPD
Heated to 50° C., added more methanol and tBME, repeated cool. Sample isolated by centrifugation analyzed by XRPD.
Attempted isolation by filtration failed; additional methanol added to dissolve gum, additional tBME added, repeated cool.
Solid isolated by centrifugation, washed with tBME (2.0 mL) and dried under vacuum for ca. 21 h at 35-40° C.
Dried material analyzed by XRPD, PLM and HPLC.

Procedure 3:
Approximately 200 mg of MTP-131 HCl weighed into 20 mL scintillation vial, dissolved in 1.4 mL of methanol at 50° C. with stirring.
Aliquots (100 µL) of tBME added slowly at 50° C. Crystallization began after 700 µL of tBME added, so held at 50° C. for 0.75 h.

Cooled from 50° C. to 5° C. at 0.1° C./min, held at 5° C. for ca. 8 h.

Sample isolated by centrifugation analyzed by XRPD.

Solid isolated by centrifugation, washed with tBME (2.0 mL) and dried under vacuum for ca. 21 h at 35-40° C.

Dried material analyzed by XRPD, PLM, TG/DTA, DSC, GVS, 1H NMR spectroscopy and HPLC.

Further drying carried out on 50 mg of material, at 40° C. (23 h), 50° C. (72 h) and 70° C. (20 h) under vacuum, with TG/DT analysis carried out after each drying condition.

Wash solution and mother liquor combined, stirred at 50° C. as additional tBME (1.5 mL) added.

Cooling repeated, yielding second batch of solid which was also isolated by centrifugation, washed with tBME (2.0 mL) and dried under vacuum for ca. 20.5 h at 35-40° C.

Second batch of dried material analyzed by XRPD and HPLC.

Example 7. Initial Characterization of MTP-131 HCl

Analysis of MTP-131 HCl by XRPD, PLM, TG/DTA, DSC, GVS, KF, HPLC-UV and HPLC-CAD was carried out in order to characterize the MTP-131 HCl and to obtain benchmark data for comparison during later studies. Characterization of the MTP-131 HCl yielded the following information:

amorphous by XRPD analysis;

non-birefringent by PLM analysis, with no clearly defined morphology;

TG analysis showed a weight loss of ca. 2.1% from the outset up to ca. 130° C., followed by weight loss of ca. 0.2% between ca. 130° C.-210° C.;

DTA showed an endothermic event at ca. 168.4° C. (onset at ca. 161.5° C.), with a small, overlapped endothermic event observed at ca. 178.8° C.;

DSC analysis showed a broad endothermic event at ca. 96.7° C. (onset at ca. 56.8° C.), likely due to solvent/water loss; a further endothermic event was observed at ca. 169.2° C. (onset at ca. 164.0° C.);

GVS analysis indicated that MTP-131 HCl was highly hygroscopic, with a mass increase of ca. 30% between 40-90% RH observed. The input solid deliquesced and adhered to the basket, so no post-GVS sample was obtained for XRPD;

contained ca. 3.2% water by KF analysis;

the purity was found to be 98.8% by HPLC analysis;

3.5 eq. of chloride were obtained by CAD analysis.

Example 8. Approximate Solubility of MTP-131 HCl

Approximate solubility values for MTP-131 HCl were estimated through a solvent addition technique, heating at 50° C. between aliquots (see Table 7).

The Following Observations and Results were Obtained:

excellent solubility in polar, protic solvents, with both methanol and methanol:water (95:5 v/v) giving solubility values of >200 mg/mL;

Reasonable solubility (ca. 67 mg/mL) was obtained in ethanol:water (95:5 v/v);

Moderate solubility (ca. 33 mg/mL) was obtained in in ethanol:DMSO (95:5 v/v);

Poor solubility (≤10 mg/mL) was obtained in all other solvent systems investigated, including acetone, dichloromethane, ethanol, 2-propanol, trifluoroethanol and all water or DMSO mixtures of acetone, acetonitrile, 2-propanol, THF and dichloromethane.

XRPD analysis was carried out on residual solids from the solubility screen, after slurrying at 50° C. overnight, with diffractograms of all residual solids being amorphous.

After fully dissolving material (using water or methanol), adding anti-solvent (tBME) and then stirring at 5° C. overnight, solid material was isolated from several solvent systems (ethanol, methanol, 2-propanol, DCM, ethanol:water (95:5 v/v), methanol:water (95:5 v/v), ethanol:DMSO (95:5 v/v) and 2-propanol:water (99:1 v/v).

XRPD analysis was carried out on these isolated solids and indicated that all were amorphous.

TABLE 7

Approximate Solubility Screen Results

| Solvent | Solubility at 50° C. (mg/mL) | Solvent Mixture | Solubility at 50° C. (mg/mL) |
| --- | --- | --- | --- |
| Acetone | <10 | Acetone:Water (95:5 v/v) | <10 |
| Dichloromethane* | <10 | Acetonitrile:Water (95:5 v/v) | <10 |
| Ethanol | 10 | Acetonitrile:Water (99:1 v/v) | <10 |
| Methanol | >200 | Ethanol:Water (95:5 v/v) | 67 |
| 2-Propanol | <10 | Methanol:Water (95:5 v/v) | >200 |
| Trifluoroethanol | <10 | 2-Propanol:Water (95:5 v/v) | <10 |
| | | 2-Propanol:Water (99:1 v/v) | <10 |
| | | THF:Water (95:5% v/v) | <10 (separated) |
| | | THF:Water (99:1 v/v) | <10 |
| | | Acetonitrile:DMSO (85:15 v/v) | <10 |
| | | DCM:DMSO (85:15 v/v) | <10 |
| | | Ethanol:DMSO (95:5% v/v) | 33 |

Note:
Dichloromethane solubility carried out at 35° C.

Example 9. Small-Scale Crystallization Screening

A. Temperature Cycling Crystallizations

Small-scale temperature cycling crystallization trials using MTP-131 HCl were carried out in 21 different solvent systems, using ethanol, methanol, trifluoromethanol, dichloromethane, acetonitrile, THF and 2-propanol. Additional solvents and antisolvents were added as required. The following results and observations were obtained from these experiments:

After the first 18 h of temperature cycling, no solids were obtained. Additional anti-solvent was added at 35° C., re-dissolving the gummed samples with additional solvent, and temperature cycling continued.

After a further 20 h of temperature cycling, solids were obtained from 2-propanol/methanol and trifluoroethanol/DMSO, but XRPD analysis indicated they were amorphous.

Further anti-solvent added to experiments, re-dissolving the gummed samples with additional solvent. Temperature cycling continued.

After a further 16 h of temperature cycling, solid obtained from DCM/methanol which was partially crystalline by XRPD, although observed to deliquesce on XRPD plate. Material was isolated by centrifugation and dried at 30° C. for 16 h.

Remaining solutions had further anti-solvent added and were stored in the fridge at ca. 5° C. for 6 days. Solid was obtained from ethanol/methanol (amorphous), 2-propanol/methanol (partially crystalline), trifluoroethanol/DMSO (amorphous) and THF/water/2-propanol (amorphous).

XRPD analysis of the solids indicated that potentially 2 different forms had been obtained from temperature cycling, although the broad diffractograms preclude definitive assignment of the patterns. The pattern obtained from 2-propanol/methanol is designated Pattern 1, while the pattern obtained from DCM/methanol is designated Pattern 2.

Results are Summarized in Table 8.

PLM analysis of the dried, partially crystalline solids from DCM/methanol and 2-propanol/methanol indicated that the material was birefringent with poorly defined morphology. Some rod-like particles were observed.

TG analysis of the dried material isolated from DCM/methanol (C4) showed a weight loss of ca. 2.9% from the outset up to ca. 130° C., followed by weight loss of ca. 2.0% between ca. 130° C.-200° C.

DTA showed an endothermic event at ca. 169.0° C. (onset at ca. 164.7° C.), with a small, overlapped endothermic event observed at ca. 181.1° C.

HPLC analysis of the dried material isolated from DCM/methanol indicated a purity value of 99.8%.

TABLE 8

Summary of Data from Temperature Cycling Crystallizations

| Cryst$^n$ | Solvent System | Final Ratio, v/v | Comments | HPLC Purity/% |
|---|---|---|---|---|
| 1 | Ethanol:Methanol | 3.3:1 | Amorphous | |
| 2 | Methanol:tBME | 1.7:1 | No solid | |
| 3 | Trifluoroethanol:Methanol | 3.3:1 | No solid | |
| 4 | Dichloromethane:Methanol | 2:1 | Partially crystalline (2) | 99.8 |
| 5 | Acetonitrile:Methanol | 1.6:1 | No solid | |
| 6 | Tetrahydrofuran:Methanol | 1.6:1 | No solid | |
| 7 | 2-Propanol:Methanol | 1.3:1 | Partially crystalline (1) | |
| 8 | Ethanol:DMSO | 5:1 | No solid | |
| 9 | Methanol:IPA | 1:1.2 | Amorphous | |
| 10 | Trifluoroethanol:DMSO | 2.7:1 | Amorphous | |
| 11 | Dichloromethane:DMSO | 2:1 | No solid | |
| 12 | Acetonitrile:DMSO | 1.9:1 | No solid | |
| 13 | Tetrahydrofuran:DMSO | 1.5:1 | No solid | |
| 14 | 2-Propanol:DMSO | 3:1 | No solid | |
| 15 | Ethanol:Water | 8.5:1 | No solid | |
| 16 | Water:MIBK:IPA | 1:2.8:2.4 | No solid | |
| 17 | Trifluoroethanol:Water | 8.5:1 | No solid | |
| 18 | Dichloromethane:DMF | 1.1:1 | No solid | |
| 19 | Acetonitrile:Water:IPA | 10:1:4 | No solid | |
| 20 | Tetrahydrofuran:Water:IPA | 10:1:6 | Amorphous | |
| 21 | 2-Propanol:Water | 6.5:1 | No solid | |

B. Cooling Crystallizations

Small-scale cooling crystallization trials using MTP-131 HCl were carried out in 20 different solvent systems, using ethanol, methanol, trifluoroethanol, dichloromethane, acetonitrile, THF, 2-propanol and water. Additional solvents and anti-solvents were added as required. The following results and observations were obtained from these experiments:

After stirring at 5° C. for ca. 6 days and one further cooling program, solids were isolated from ethanol/methanol, THF/methanol and methanol/ethyl acetate/water. After isolating by centrifugation and analyzing by XRPD, these solids were determined to be crystalline.

The crystalline solids isolated from the cooling crystallizations were consistent with Pattern 1, except for the solid isolated from trifluoroethanol/methanol/tBME which was consistent with Pattern 2. The poor crystallinity of the Pattern 2 material isolated during crystallization screening makes definitive assignment difficult.

All crystalline solids were dried under vacuum at 30° C. for ca. 23 h. The drying did not appear to have a detrimental effect on the crystallinity of the solids.

Results are Summarized in Table 9.

PLM analysis of the dried, crystalline solids indicated that the material was birefringent with poorly defined morphology. Some aggregation was observed.

TG analysis of the dried material isolated from methanol/tBME (C2) showed a weight loss of ca. 2.0% from the outset up to ca. 130° C., followed by weight loss of ca. 1.4% between ca. 130° C.-210° C.

DTA showed an endothermic event at ca. 194.3° C.

TG analysis of the dried material isolated from methanol/2-propanol (C8) showed a weight loss of ca. 2.1% from the outset up to ca. 130° C., followed by weight loss of ca. 0.9% between ca. 130° C.-210° C.

DTA showed an endothermic event at ca. 180.9° C. (onset at ca. 176.0° C.).

HPLC analysis of the dried, crystalline solids indicated purity values of 99.1-99.6%.

TABLE 9

Experimental Details for Small-Scale Cooling Crystallization Trials

| Cryst$^n$ | Solvent System | Final Ratio, v/v | Comments | HPLC Purity/% |
|---|---|---|---|---|
| 1 | Ethanol:Methanol | 4.75:1 | Crystalline (1) | 99.3 |
| 2 | Methanol:tBME | 1.75:1 | Crystalline (1) | 99.2 |
| 3 | Trifluoroethanol:Methanol:tBME | 5.25:2.5:1 | Partially crystalline (2) | 99.5 |
| 4 | Acetonitrile:Methanol | 1.1:1 | Crystalline (1) | 99.6 |
| 5 | Tetrahydrofuran:Methanol | 1.1:1 | Crystalline (1) | 99.1 |
| 6 | 2-Propanol:Methanol | 1.25:1 | Crystalline (1) | 99.2 |
| 7 | Ethanol:DMSO:tBME | 10.5:2:1 | No solid | |
| 8 | Methanol:IPA | 1.1:1 | Partially crystalline (1) | 99.2 |
| 9 | Trifluoroethanol:DMSO | 3.8:1 | Amorphous | |
| 10 | Acetonitrile:DMSO:tBME | 6.5:3:1 | Gum | |
| 11 | Tetrahydrofuran:DMSO:tBME | 6.5:3:1 | Gum | |
| 12 | 2-Propanol:DMSO:tBME | 8.5:2:1 | Gum | |
| 13 | Ethanol:Water:tBME | 11.5:1:1 | No solid | |
| 14 | Methanol:Ethyl acetate:Water | 12.5:10:1 | Crystalline (1) | |
| 15 | Trifluoroethanol:Water:tBME | 10.5:1:1 | No solid | |
| 16 | Acetonitrile:Water:tBME | 8.5:2:1 | Separated | |
| 17 | Tetrahydrofuran:Water:IPA:tBME | 7.5:1.5:1:1 | No solid | |
| 18 | 2-Propanol:Water:tBME | 10.5:1:1 | Gum | |
| 19 | Methanol:tBME | 1.75:1 | Partially crystalline (1) | 99.4 |
| 20 | Water | | No solid | |

C. Evaporative Crystallizations

After re-dissolving the slurries from the solubility/ASA experiments, solutions were allowed to evaporate at ambient temperature. The following results and observations were obtained from these experiments:

Solid material was isolated from all experiments, except those containing DMSO.

XRPD analysis of the isolated solids indicated that all were amorphous.

Example 10. Crystallization Scale-Up

Crystallization scale-up was carried out with MTP-131 HCl-040-2) on a 200 mg scale, using methanol and tBME. The following results and observations were obtained from these experiments:

In Crystallization 1, the solid which crystallized initially (2 h) was consistent with the diffractogram obtained from the small-scale experiment, but had lower crystallinity. The crystallinity was improved by re-crystallizing further.

In Crystallization 2, the solid which crystallized initially (0.75 h) was consistent with the diffractogram obtained from the small-scale experiment, but had lower crystallinity. The crystallinity was improved by re-crystallizing further.

Attempts to isolate the material from Crystallization 2 by filtration failed because it became sticky on the filter paper, likely due to the hygroscopic nature of the material. Isolation through centrifugation was successful, with the mother liquor and wash solution decanted after centrifuging.

In Crystallization 3, the solid which crystallized initially (16 h) was consistent with the diffractogram obtained from the small-scale experiment. 0.14 g, 72% isolated yield. This material was used for full characterization.

XRPD analysis of all samples taken during C1-3 and of the dried samples indicated that the same pattern as the small-scale crystallizations in that solvent system had been obtained (Pattern 1).

PLM analysis of both the slurry and the dried material from C1 indicated that the recrystallized material was birefringent by PLM analysis, with rod-like morphology. Some aggregation was observed.

PLM analysis of both the slurry and the dried material from C2 indicated that the recrystallized material was slightly birefringent by PLM analysis, with poorly defined morphology.

PLM analysis of both the slurry and the dried material from C3 indicated that the recrystallized material was birefringent by PLM analysis, with a rod-like morphology. Some aggregation was observed.

TG analysis of the C3 dried material (21 h at 26-40° C.) showed weight loss of ca. 2.2% from the outset up to ca. 150° C., followed by weight loss of ca. 1.4% between ca. 150° C.-200° C.

(Note: 1 mol eq. of H2O would be 2.4 wt %).

DTA showed an endothermic event at ca. 219.1° C. (onset at ca. 203.8° C.), close to the onset of decomposition.

TG analysis of the C3 dried material (21 h at <40° C., 23 h at 40° C.) showed weight loss of ca. 2.6% from the outset up to ca. 150° C., followed by weight loss of ca. 1.0% between ca. 150° C.-200° C.

DTA showed an endothermic event at ca. 219.6° C. (onset at ca. 207.7° C.), close to the onset of decomposition.

TGA of the C3 dried material (21 h at <40° C., 23 h at 40° C., 72 h at 50° C.) showed weight loss of ca. 2.1% from the outset up to ca. 150° C., followed by weight loss of ca. 1.1% between ca. 150° C.-220° C.

DTA showed an endothermic event at ca. 219.8° C. (onset at ca. 207.4° C.), close to the onset of decomposition.

TGA of the C3 dried material (21 h at <40° C., 23 h at 40° C., 72 h at 50° C., 20 h at 70° C.) showed weight loss of ca. 2.9% from the outset up to ca. 160° C., followed by weight loss of ca. 0.9% between ca. 160° C.-220° C.

DTA showed an endothermic event at ca. 217.1° C. (onset at ca. 207.6° C.), close to the onset of decomposition.

DSC analysis of the C3 dried material (21 h at <40° C.) showed a broad endothermic event at ca. 81.2° C.

(onset at ca. 48.3° C.), likely due to solvent/water loss. Further endothermic events were observed at ca. 188.8° C. (onset at ca. 174.2° C.) and at ca. 215.0° C. (onset at ca. 204.5° C.).

GVS analysis of the C3 dried material (21 h at <40° C.) indicated that the re-crystallized material was highly hygroscopic, with a mass increase of ca. 30% between 40-90% RH observed. The material deliquesced and adhered to the basket, so no post-GVS sample was obtained for XRPD.

The re-crystallized material contained ca. 6.9% water by KF analysis. However, the hygroscopic nature of the material and low solubility in the KF medium may have resulted in absorption of moisture during the dissolution step, prior to analysis.

The 1H NMR spectrum of the re-crystallized material was consistent with the structure of the compound. The spectrum indicated that there was ca. 0.4 wt % tBME present and so the weight loss in the TGA is most likely due to water.

HPLC analysis of the dried material isolated from C1 indicated a purity value of 99.2% (cf. 98.8% for the input amorphous material). 2.5 eq. of chloride were obtained by CAD analysis.

HPLC analysis of the dried material isolated from C2 indicated a purity value of 98.6%.

HPLC analysis of the dried material isolated from C3 indicated a purity value of 99.0%. 3.3 eq. of chloride were obtained by CAD analysis.

The second batch of material isolated from C3 had significantly lower purity: 97.9% and the chloride content was determined to be 3.9 eq.

Example 11. Crystalline Tris-HCl Salt of MTP-131—XRPD Peak List

TABLE 10

| Pos. [°2θ] | d-spacing [A] | Height [cts] | Rel. Int. [%] |
|---|---|---|---|
| 5.6826 | 15.55252 | 48.89 | 5.06 |
| 6.669 | 13.25428 | 16.7 | 1.73 |
| 8.1507 | 10.84783 | 650.66 | 67.29 |
| 9.2697 | 9.54072 | 154.41 | 15.97 |
| 9.8231 | 9.00438 | 277.37 | 28.68 |
| 11.0495 | 8.00758 | 264.45 | 27.35 |
| 11.4729 | 7.713 | 393.18 | 40.66 |
| 12.3925 | 7.14266 | 360.31 | 37.26 |
| 12.8405 | 6.89444 | 63.27 | 6.54 |
| 13.6472 | 6.48865 | 237.2 | 24.53 |
| 14.3699 | 6.16392 | 107.3 | 11.1 |
| 14.8755 | 5.95554 | 245.56 | 25.39 |
| 15.5909 | 5.68384 | 369.87 | 38.25 |
| 15.8566 | 5.58918 | 690.32 | 71.39 |
| 17.1543 | 5.16919 | 226.03 | 23.38 |
| 17.5374 | 5.05713 | 195.25 | 20.19 |
| 17.953 | 4.94097 | 47.6 | 4.92 |
| 18.525 | 4.78968 | 58.51 | 6.05 |
| 18.9247 | 4.68942 | 87.39 | 9.04 |
| 19.3114 | 4.59638 | 76.49 | 7.91 |
| 19.6517 | 4.51754 | 125.18 | 12.95 |
| 20.1474 | 4.40749 | 317.33 | 32.82 |
| 20.3935 | 4.35487 | 89.76 | 9.28 |
| 20.6086 | 4.3099 | 83.34 | 8.62 |
| 21.1328 | 4.20415 | 68.92 | 7.13 |
| 21.8535 | 4.06712 | 319.84 | 33.08 |
| 22.1439 | 4.01443 | 737.79 | 76.3 |
| 22.6006 | 3.93432 | 204.99 | 21.2 |
| 23.0153 | 3.86436 | 966.96 | 100 |
| 23.4697 | 3.79057 | 560.81 | 58 |
| 23.9736 | 3.71203 | 182.25 | 18.85 |
| 24.2292 | 3.67344 | 181.59 | 18.78 |

TABLE 10-continued

| Pos. [°2θ] | d-spacing [A] | Height [cts] | Rel. Int. [%] |
|---|---|---|---|
| 24.8488 | 3.58324 | 192.35 | 19.89 |
| 25.46 | 3.49858 | 152.72 | 15.79 |
| 25.8659 | 3.44459 | 116.17 | 12.01 |
| 26.4139 | 3.37436 | 205.95 | 21.3 |
| 26.945 | 3.30905 | 134.94 | 13.96 |
| 27.4489 | 3.24943 | 407.87 | 42.18 |
| 27.9725 | 3.18979 | 284.45 | 29.42 |
| 28.1692 | 3.16796 | 237.71 | 24.58 |
| 28.7691 | 3.10326 | 99.86 | 10.33 |
| 29.6808 | 3.00998 | 36.29 | 3.75 |
| 30.7678 | 2.90607 | 48.38 | 5 |
| 31.7169 | 2.82124 | 134.12 | 13.87 |
| 33.0072 | 2.71384 | 72.56 | 7.5 |
| 33.8578 | 2.64759 | 76.16 | 7.88 |

What is claimed is:

1. A crystalline form of a bis-(hydrochloride) salt of Compound (I),

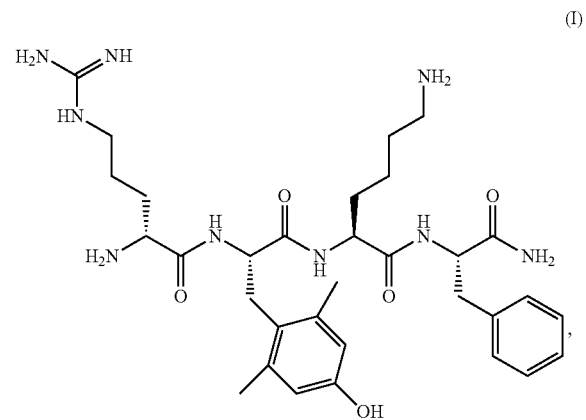 [SMILES: Cc1cc(O)cc(C)c1C[C@H](NC(=O)[C@H](N)CCCNC(=N)N)C(=O)N[C@@H](CCCCN)C(=O)N[C@@H](Cc1ccccc1)C(N)=O]

(I)

wherein said crystalline form has peaks in its XRPD pattern at values of two theta as listed in Table 2A:

TABLE 2A

| 2θ (°) | d spacing (A°) | Height (cps) | Relative intensity (%) |
|---|---|---|---|
| 6.40 | 13.79726 | 1343 | 28 |
| 6.98 | 12.65711 | 406 | 9 |
| 7.88 | 11.20719 | 160 | 3 |
| 9.05 | 9.76484 | 112 | 2 |
| 9.84 | 8.97904 | 1550 | 33 |
| 10.18 | 8.67918 | 186 | 4 |
| 11.65 | 7.58843 | 340 | 7 |
| 13.06 | 6.77213 | 4732 | 100 |
| 16.88 | 5.24746 | 715 | 15 |
| 19.09 | 4.64608 | 790 | 17 |
| 20.61 | 4.30611 | 289 | 6 |
| 24.21 | 3.67305 | 113 | 2 |
| 24.84 | 3.58126 | 433 | 9 |
| 26.33 | 3.38163 | 298 | 6 |
| 27.44 | 3.24777 | 327 | 7 |
| 28.59 | 3.11934 | 158 | 3 |
| 29.73 | 3.00251 | 480 | 10. |

2. A crystalline form of a bis-(hydrochloride) salt of Compound (I),

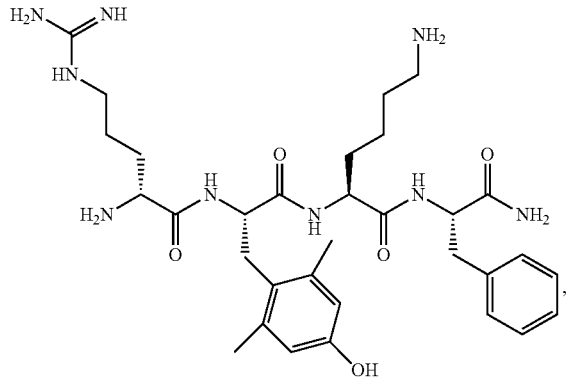

(I)

wherein said crystalline form has peaks in its XRPD pattern as shown in FIG. 2.

3. A crystalline form of a bis-(hydrochloride) salt of Compound (I),

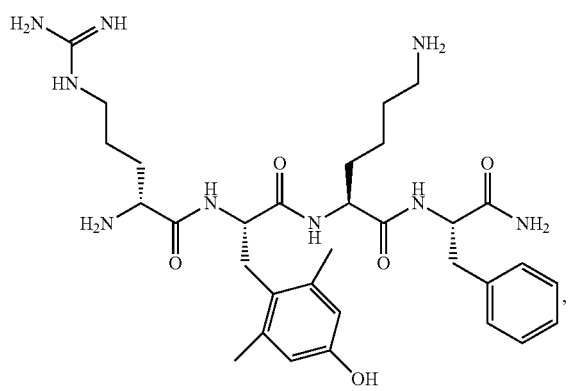

(I)

wherein said crystalline form has peaks in its XRPD pattern at values of two theta (° 2) of: 6.4, 9.8, 13.1, 16.9, 19.1, and 29.7.

4. The crystalline form of claim 3, wherein said crystalline form has peaks in its XRPD pattern at values of two theta (° 2) of: 6.4, 7.0, 7.9, 9.1, 9.8, 10.2, 11.7, 13.1, 16.9, 19.1, 20.6, 24.2, 24.8, 26.3, 27.4, 28.6, and 29.7.

5. A crystalline form of a tris-(hydrochloride) salt of Compound (I),

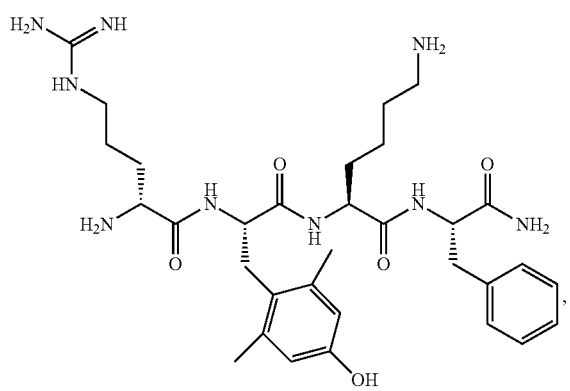

(I)

wherein said crystalline form has peaks in its XRPD pattern at values of two theta as listed in Table 10A:

TABLE 10A

| Pos. [°2θ] | d-spacing [Å] | Height [cts] | Rel. Int. [%] |
|---|---|---|---|
| 5.6826 | 15.55252 | 48.89 | 5.06 |
| 6.669 | 13.25428 | 16.7 | 1.73 |
| 8.1507 | 10.84783 | 650.66 | 67.29 |
| 9.2697 | 9.54072 | 154.41 | 15.97 |
| 9.8231 | 9.00438 | 277.37 | 28.68 |
| 11.0495 | 8.00758 | 264.45 | 27.35 |
| 11.4729 | 7.713 | 393.18 | 40.66 |
| 12.3925 | 7.14266 | 360.31 | 37.26 |
| 12.8405 | 6.89444 | 63.27 | 6.54 |
| 13.6472 | 6.48865 | 237.2 | 24.53 |
| 14.3699 | 6.16392 | 107.3 | 11.1 |
| 14.8755 | 5.95554 | 245.56 | 25.39 |
| 15.5909 | 5.68384 | 369.87 | 38.25 |
| 15.8566 | 5.58918 | 690.32 | 71.39 |
| 17.1543 | 5.16919 | 226.03 | 23.38 |
| 17.5374 | 5.05713 | 195.25 | 20.19 |
| 17.953 | 4.94097 | 47.6 | 4.92 |
| 18.525 | 4.78968 | 58.51 | 6.05 |
| 18.9247 | 4.68942 | 87.39 | 9.04 |
| 19.3114 | 4.59638 | 76.49 | 7.91 |
| 19.6517 | 4.51754 | 125.18 | 12.95 |
| 20.1474 | 4.40749 | 317.33 | 32.82 |
| 20.3935 | 4.35487 | 89.76 | 9.28 |
| 20.6086 | 4.3099 | 83.34 | 8.62 |
| 21.1328 | 4.20415 | 68.92 | 7.13 |
| 21.8535 | 4.06712 | 319.84 | 33.08 |
| 22.1439 | 4.01443 | 737.79 | 76.3 |
| 22.6006 | 3.93432 | 204.99 | 21.2 |
| 23.0153 | 3.86436 | 966.96 | 100 |
| 23.4697 | 3.79057 | 560.81 | 58 |
| 23.9736 | 3.71203 | 182.25 | 18.85 |
| 24.2292 | 3.67344 | 181.59 | 18.78 |
| 24.8488 | 3.58324 | 192.35 | 19.89 |
| 25.46 | 3.49858 | 152.72 | 15.79 |
| 25.8659 | 3.44459 | 116.17 | 12.01 |
| 26.4139 | 3.37436 | 205.95 | 21.3 |
| 26.945 | 3.30905 | 134.94 | 13.96 |
| 27.4489 | 3.24943 | 407.87 | 42.18 |
| 27.9725 | 3.18979 | 284.45 | 29.42 |
| 28.1692 | 3.16796 | 237.71 | 24.58 |
| 28.7691 | 3.10326 | 99.86 | 10.33 |
| 29.6808 | 3.00998 | 36.29 | 3.75 |
| 30.7678 | 2.90607 | 48.38 | 5 |
| 31.7169 | 2.82124 | 134.12 | 13.87 |
| 33.0072 | 2.71384 | 72.56 | 7.5 |
| 33.8578 | 2.64759 | 76.16 | 7.88. |

6. A crystalline form of a tris-(hydrochloride) salt of Compound (I),

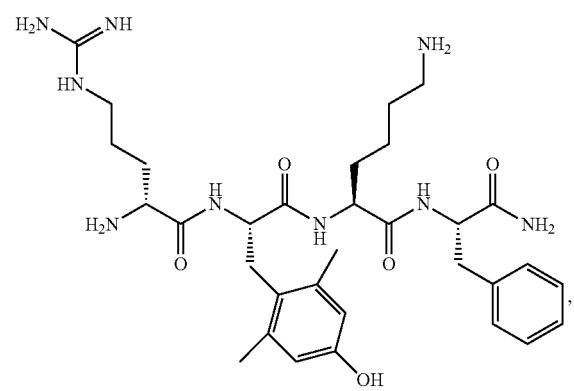

(I)

wherein said crystalline form has peaks in its XRPD pattern as shown in FIG. 9.

7. A crystalline form of a tris-(hydrochloride) salt of Compound (I),

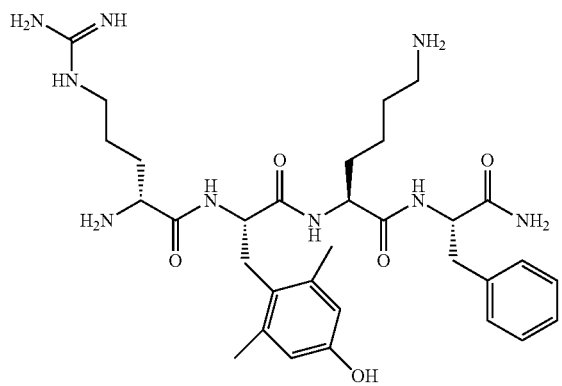

(I)

wherein said crystalline form has peaks in its XRPD pattern at values of two theta (° 2) of: 8.1, 11.5, 15.6, 15.9, 22.1, 23.0, and 27.4.

8. The crystalline form of claim 7, wherein said crystalline form has peaks in its XRPD pattern at values of two theta (° 2) of: 8.1, 9.8, 11.0, 11.5, 12.4, 14.9, 15.6, 15.9, 20.1, 21.8, 22.1, 23.0, 27.4, and 28.0.

9. A composition, comprising the crystalline form of claim 1.

10. A process for making a pharmaceutical composition comprising Compound (I),

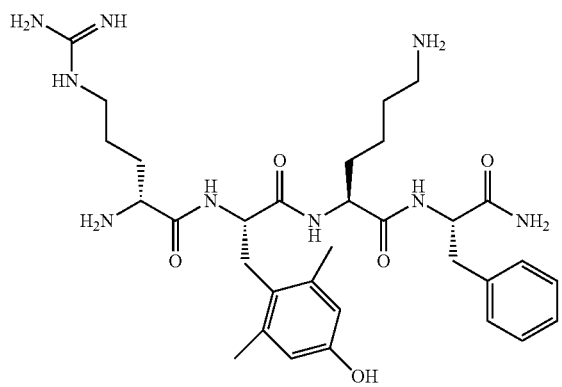

(I)

which comprises dissolving the crystalline form of claim 1.

11. A process for making a pharmaceutical composition comprising Compound (I),

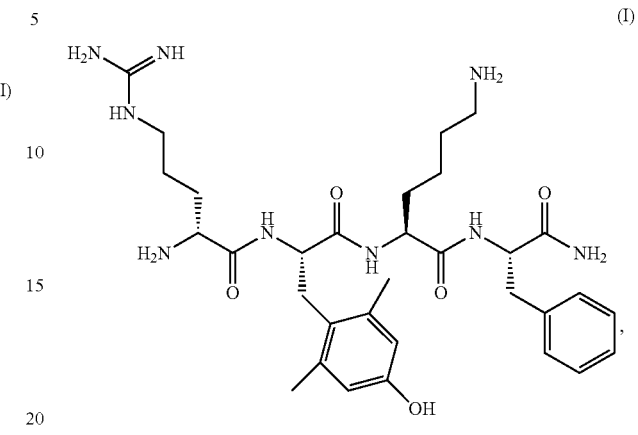

(I)

which comprises dissolving the crystalline form of claim 5.

12. A process for making a pharmaceutical composition comprising Compound (I),

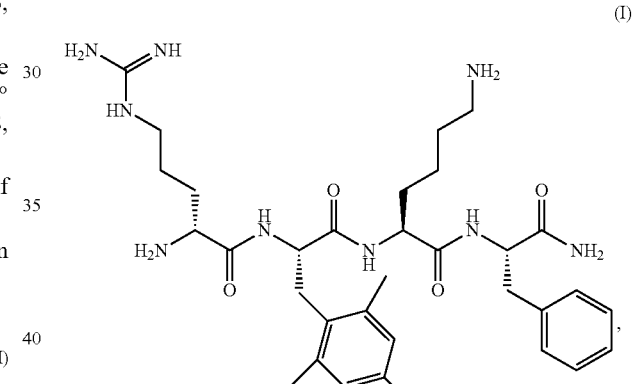

(I)

which comprises dissolving the crystalline form of claim 1.

13. A composition, comprising the crystalline form of claim 2.

14. A composition, comprising the crystalline form of claim 3.

15. A composition, comprising the crystalline form of claim 4.

16. A composition, comprising the crystalline form of claim 5.

17. A composition, comprising the crystalline form of claim 6.

18. A composition, comprising the crystalline form of claim 7.

19. A composition, comprising the crystalline form of claim 8.

* * * * *

UNITED STATES PATENT AND TRADEMARK OFFICE
CERTIFICATE OF CORRECTION

PATENT NO. : 10,676,506 B2
APPLICATION NO. : 16/259575
DATED : June 9, 2020
INVENTOR(S) : Scott M. Duncan Page 1 of 1

It is certified that error appears in the above-identified patent and that said Letters Patent is hereby corrected as shown below:

In the Claims

In Claim 3, at Column 33, Line numbers 41-43:
"wherein said crystalline form has peaks in its XRPD pattern at values of two theta (° 2) of:
6.4, 9.8, 13.1, 16.9, 19.1, and 29.7"
Should read:
-- wherein said crystalline form has peaks in its XRPD pattern at values of two theta (°2θ) of:
6.4, 9.8, 13.1, 16.9, 19.1, and 29.7 --.

In Claim 4, at Column 33, Line numbers 45-48:
"wherein said crystalline form has peaks in its XRPD pattern at values of two theta (° 2) of:
6.4, 7.0, 7.9, 9.1, 9.8, 10.2, 11.7, 13.1, 16.9, 19.1, 20.6, 24.2, 24.8, 26.3, 27.4, 28.6, and 29.7"
Should read:
-- wherein said crystalline form has peaks in its XRPD pattern at values of two theta (°2θ) of:
6.4, 7.0, 7.9, 9.1, 9.8, 10.2, 11.7, 13.1, 16.9, 19.1, 20.6, 24.2, 24.8, 26.3, 27.4, 28.6, and 29.7 --.

In Claim 7, at Column 35, Line numbers 27-29:
"wherein said crystalline form has peaks in its XRPD pattern at values of two theta (° 2) of:
8.1, 11.5, 15.6, 15.9, 22.1, 23.0, and 27.4"
Should read:
-- wherein said crystalline form has peaks in its XRPD pattern at values of two theta (°2θ) of:
8.1, 11.5, 15.6, 15.9, 22.1, 23.0, and 27.4 --.

In Claim 8, at Column 35, Line numbers 30-33:
"wherein said crystalline form has peaks in its XRPD pattern at values of two theta (° 2) of:
8.1, 9.8, 11.0, 11.5, 12.4, 14.9, 15.6, 15.9, 20.1, 21.8, 22.1, 23.0, 27.4, and 28.0"
Should read:
-- wherein said crystalline form has peaks in its XRPD pattern at values of two theta (°2θ) of:
8.1, 9.8, 11.0, 11.5, 12.4, 14.9, 15.6, 15.9, 20.1, 21.8, 22.1, 23.0, 27.4, and 28.0 --.

Signed and Sealed this
Thirteenth Day of October, 2020

Andrei Iancu
*Director of the United States Patent and Trademark Office*